US011083588B2

(12) United States Patent
Muir et al.

(10) Patent No.: US 11,083,588 B2
(45) Date of Patent: Aug. 10, 2021

(54) METHODS AND APPARATUSES FOR TRIALING A HUMERAL HEAD

(71) Applicant: Biomet Manufacturing, LLC, Warsaw, IN (US)

(72) Inventors: Nicholas Muir, Winona Lake, IN (US); Ravikumar Varadarajan, Warsaw, IN (US); Nathan A. Winslow, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 58 days.

(21) Appl. No.: 15/846,624

(22) Filed: Dec. 19, 2017

(65) Prior Publication Data

US 2018/0168815 A1 Jun. 21, 2018

Related U.S. Application Data

(60) Provisional application No. 62/437,192, filed on Dec. 21, 2016.

(51) Int. Cl.
*A61F 2/40* (2006.01)
*A61F 2/30* (2006.01)
(Continued)

(52) U.S. Cl.
CPC .......... *A61F 2/4014* (2013.01); *A61F 2/4657* (2013.01); *A61F 2/4684* (2013.01);
(Continued)

(58) Field of Classification Search
CPC ...................... A61F 2/4081; A61F 2/40; A61F 2002/30332; A61F 2/4612; A61F 2/4014;
(Continued)

(56) References Cited

U.S. PATENT DOCUMENTS 5,507,824 A * 4/1996 Lennox ................. A61F 2/4609
623/22.25
6,673,114 B2 1/2004 Hartdegen et al.
(Continued)

FOREIGN PATENT DOCUMENTS

CN 110087586 A 8/2019
WO 0182843 11/2001
(Continued)

OTHER PUBLICATIONS

"International Application Serial No. PCT US2017 067244, International Search Report dated Mar. 27, 2018", 7 pgs.
(Continued)

*Primary Examiner* — Ann Schillinger
(74) *Attorney, Agent, or Firm* — Schwegman Lundberg & Woessner, P.A.

(57) ABSTRACT

A system for aligning components of a prosthetic includes a mounting plate, a fastener and an adapter coupling plate. The mounting plate comprises: a first major surface; a second major surface opposing the first major surface; an adapter accommodation hole extending through the mounting plate; and sizing indicia located on the second major surface. The fastener extends from the mounting plate. The adapter coupling plate comprises: a third major surface; a fourth major surface opposing the third major surface; an adapter coupling hole extending through the adapter coupling plate and surrounded by the adapter accommodation hole; and an indicator located on the fourth major surface to point to the sizing indicia on the mounting plate. The adapter coupling plate can be slidable along a slot surrounding the fastener or a tongue and groove system connecting the adapter coupling plate and the mounting plate and locked via the fastener.

29 Claims, 17 Drawing Sheets

(51) Int. Cl.
*A61F 2/28* (2006.01)
*A61F 2/46* (2006.01)

(52) U.S. Cl.
CPC .............. *A61F 2002/30331* (2013.01); *A61F 2002/30362* (2013.01); *A61F 2002/30507* (2013.01); *A61F 2002/30537* (2013.01); *A61F 2002/30604* (2013.01); *A61F 2002/30617* (2013.01); *A61F 2002/4018* (2013.01); *A61F 2002/4029* (2013.01); *A61F 2002/4037* (2013.01); *A61F 2002/4051* (2013.01); *A61F 2002/4062* (2013.01)

(58) Field of Classification Search
CPC .................. A61F 2/4059; A61F 2/4684; A61F 2002/30616; A61F 2002/3652; A61F 2002/4085; A61F 2/30734; A61F 2/32; A61F 2/34; A61F 2/3609; A61F 2/3662; A61F 2/3859; A61F 2/4003; A61F 2/4657; A61F 2002/30736; A61F 2002/3085

See application file for complete search history.

(56) References Cited

U.S. PATENT DOCUMENTS

| | | | |
|---|---|---|---|
| 6,736,852 B2 | 5/2004 | Callaway et al. | |
| 7,097,663 B1* | 8/2006 | Nicol | A61F 2/4014 623/19.12 |
| 7,431,736 B2 | 10/2008 | Maroney et al. | |
| 7,537,618 B2* | 5/2009 | Collazo | A61F 2/4684 623/19.14 |
| 8,052,758 B1* | 11/2011 | Winslow | A61F 2/4657 623/22.42 |
| 8,647,387 B2 | 2/2014 | Winslow | |
| 2001/0053935 A1* | 12/2001 | Hartdegen | A61F 2/4014 623/19.12 |
| 2002/0016634 A1 | 2/2002 | Maroney et al. | |
| 2002/0120339 A1* | 8/2002 | Callaway | A61F 2/4014 623/19.14 |
| 2005/0033443 A1* | 2/2005 | Blatter | A61F 2/4014 623/19.14 |
| 2007/0173945 A1 | 7/2007 | Wiley et al. | |
| 2007/0198094 A1 | 8/2007 | Berelsman et al. | |
| 2009/0270993 A1 | 10/2009 | Maisonneuve et al. | |
| 2010/0331993 A1* | 12/2010 | Gradl | A61F 2/30 623/23.4 |
| 2011/0054624 A1 | 3/2011 | Iannotti | |
| 2015/0250601 A1 | 9/2015 | Humphrey | |

FOREIGN PATENT DOCUMENTS

| | | | |
|---|---|---|---|
| WO | 2012125795 | 9/2012 | |
| WO | 2014138061 | 9/2014 | |
| WO | WO-2018106633 A1 * | 6/2018 | ........... A61F 2/4014 |

OTHER PUBLICATIONS

"International Application Serial No. PCT US2017 067244, Written Opinion dated Mar. 27, 2018", 9 pgs.

"European Application Serial No. 17829468.2, Response to Communication pursuant to Rules 161(1) and 162 EPC filed Feb. 24, 2020", 22 pgs.

"European Application Serial No. 17829468.2, Communication Pursuant to Article 94(3) EPC dated Aug. 20, 2020", 4 pages.

"Chinese Application Serial No. 201780079069.X, Office Action dated Nov. 2, 2020", with English translation, 26 pages.

"European Application Serial No. 17829468.2, Response filed Jan. 6, 2021 to Communication Pursuant to Article 94(3) EPC dated Aug. 20, 2020", 31 pages.

"Chinese Application Serial No. 201780079069.X, Response filed Mar. 2, 2021 to Office Action dated Nov. 2, 2020", w English claims, 21 pages.

* cited by examiner

METHODS AND APPARATUSES FOR TRIALING A HUMERAL HEAD

CLAIM OF PRIORITY

This application claims the benefit of priority to U.S. Provisional Application Ser. No. 62/437,192, filed on Dec. 21, 2016, which is incorporated herein by reference in its entirety.

TECHNICAL FIELD

This document pertains generally, but not by way of limitation, to systems and methods for planning and performing arthroplasty procedures. More particularly, this disclosure relates to, but not by way of limitation, intraoperative planning techniques for selecting the size of a prosthetic device component for a patient into which the prosthetic device component will be implanted.

BACKGROUND

A shoulder joint comprises the juncture of the scapula, the clavicle and the humerus. The head of the humerus fits into a shallow socket of the scapula called the glenoid fossa to form a mobile joint. When the joint is articulated, the humeral head moves in the glenoid fossa to provide a wide range of motion. The shoulder joint may suffer from various maladies including rheumatoid arthritis, osteoarthritis, rotator cuff arthropathy, avascular necrosis, bone fracture or failure of previous joint implants. If severe joint damage occurs and no other means of treatment is found to be effective, then shoulder reconstruction may be necessary.

A shoulder joint prosthesis generally includes the replacement of the ball (glenosphere) of the humerus and, optionally, the socket (glenoid) of the shoulder blade with specially designed artificial components. The bio-kinematics, and thus the range of motion in the shoulder vary greatly among prospective patients for reconstruction shoulder surgery. The humeral component typically can have a metal shaft or stem with a body portion that can be embedded in the resected humerus and a generally hemispherical head portion supported on the stem. The head portion can slidingly engage a glenoid implant on the glenoid fossa. During reconstructive surgery, the components of the prosthesis can be matched with the bio-kinematics of the patient in an effort to maintain the natural range of motion of a healthy shoulder joint. Thus, a shoulder prosthesis design can be readily adaptable to a wide range of bio-kinematics for prospective patients.

In this regard, shoulder prostheses are generally available as either unitary structures or modular components. With unitary shoulder prosthesis, a large inventory of differently sized prostheses must sometimes be maintained to accommodate the different bone sizes and joint configurations of the prospective patients. With such unitary shoulder prosthesis, the patient can typically be evaluated by X-ray to determine approximate sizes of prostheses needed for reconstruction. A number of differently sized prostheses can be selected as possible candidates based upon this preliminary evaluation. Final selection of the appropriately sized prosthesis can be made during the surgery. With unitary shoulder prosthesis, each design can represent a compromise that is unable to achieve all of the natural range of motion of a healthy shoulder joint because of the fixed geometric configuration in their design.

Modular prostheses systems that can reduce the need to maintain large inventories of various sized components are well known in the art. Conventionally, a humeral prosthesis can include two components: a humeral stem component and a spherical head releasably coupled to the stem. Alternatively, a three component design is known in which the stem and spherical head are interconnected with an adapter. In either of the two-piece or three-piece designs, a radial offset or angulator inclination of the head relative to the stem can be provided in individual components. Different radial offsets or angular inclinations are achieved through the use of different adapters or heads. In this regard, conventional modular shoulder prosthesis kits can include multiple redundant components such as adapters and heads to achieve a range of prosthetic options.

While providing an advantage over the unitary design in reducing the number of components needed, a rather large inventory of head components and/or adapter components must sometimes be maintained to provide the desired range of geometric configurations with the conventional modular shoulder prostheses. These components can be readily adaptable to provide a range of geometric configurations, i.e. radial offsets of angular inclination while minimizing the number of components required.

Examples of humeral head trialing devices are described in U.S. Pat. No. 8,647,387 to Winslow, U.S. Pat. No. 7,431,736 to Maroney et al., U.S. Pat. No. 6,736,852 to Callaway et al., U.S. Pat. No. 6,673,114 to Hartdegen et al., and U.S. Pub. No. 2016/0030187 to Sperling et al.

OVERVIEW

The present inventors have recognized, among other things, that a problem to be solved relates to the need for surgeons to have to select a proper size and manually adjust the location and orientation of a humeral head and a corresponding humeral head trial, which can typically involve the movement of several components that are intricately attached to each other, in order to select a properly-sized unitary or modular shoulder prosthesis. These components typically can be manually held together in place in order to make the proper reading of the size of the humeral head trial. Thus, the surgeon can be left with needing to make several estimates of the humeral head size while holding the components in place.

The present subject matter can help provide a solution to various problems associated with the trialing of a humeral head by providing a trialing assembly that can be used to couple humeral stems or humeral adapters with multiple humeral head trials. The trialing assembly can be locked in place without removing the humeral head trial from the anatomy to ensure accurate readings are taken from the assembly and a proper head size is selected. The trialing assembly can be easily assembled and disassembled, cleaned and reused, thereby minimizing the number of components and instruments that must be maintained in inventory.

In an example, the present subject matter can help provide a solution to this problem, such as by providing a system for aligning a prosthetic head implant with a prosthetic stem that can comprise a mounting plate, a first fastener and an adapter coupling plate. The mounting plate can comprise: a first major surface; a second major surface opposing the first major surface; an adapter accommodation hole extending through from the first major surface to the second major surface; and sizing indicia located on the second major surface. The first fastener can extend from the mounting plate. The adapter coupling plate can be slidably engaged with the mounting plate and can comprise: a third major surface facing in a direction of the first major surface, a fourth major surface opposing the third major surface; an adapter coupling hole extending through from the third major surface to the fourth major surface, the adapter coupling hole surrounded by the adapter accommodation hole; and an indicator located on the fourth major surface to point to various portions of the sizing indicia as the adapter coupling plate slides against the mounting plate at the first slot.

In another example, a system for aligning a prosthetic head implant with a prosthetic stem can comprise: a mounting plate, a slide post, a prosthetic head and an adapter coupling plate. The slide post can extend through the mounting plate in an adjustable manner. The prosthetic head can be stationarily coupled to the mounting plate and have an access hole aligned with the slide post. The adapter coupling plate can be slideably engaged with the mounting plate via the slide post. The slide post can be adjusted from an exterior of the prosthetic head component through the access hole to immobilize the adapter coupling plate relative to the mounting plate.

In yet another example, a system for aligning a prosthetic head component with a prosthetic stem can comprise: a mounting plate; a fastener, a prosthetic head, an adapter coupling plate and a tongue and groove system. The fastener can extend from the mounting plate in an adjustable manner. The prosthetic head can be stationarily coupled to the mounting plate and have an access hole aligned with the fastener. The tongue and groove system can slideably connect the mounting plate and the adapter coupling plate. The fastener can be adjusted from an exterior of the prosthetic head component through the access hole to immobilize the adapter coupling plate relative to the mounting plate.

In still another example, a method for aligning a prosthetic head component with a prosthetic stem can comprise: attaching a mounting plate of a trialing device to a prosthetic head component, the trialing device further including an adapter coupling plate; inserting a neck of a prosthetic stem into the adapter coupling plate; sliding the mounting plate of the trialing device relative to the adapter coupling plate to a adjust a position of the prosthetic head component relative to the neck of the prosthetic stem; and from outside of the prosthetic head, adjusting a fastener connected to the mounting plate to immobilize a position of the adapter coupling plate to lock the position.

This overview is intended to provide an overview of subject matter of the present patent application. It is not intended to provide an exclusive or exhaustive explanation of the invention. The detailed description is included to provide further information about the present patent application.

DETAILED DESCRIPTION

Figure 1:
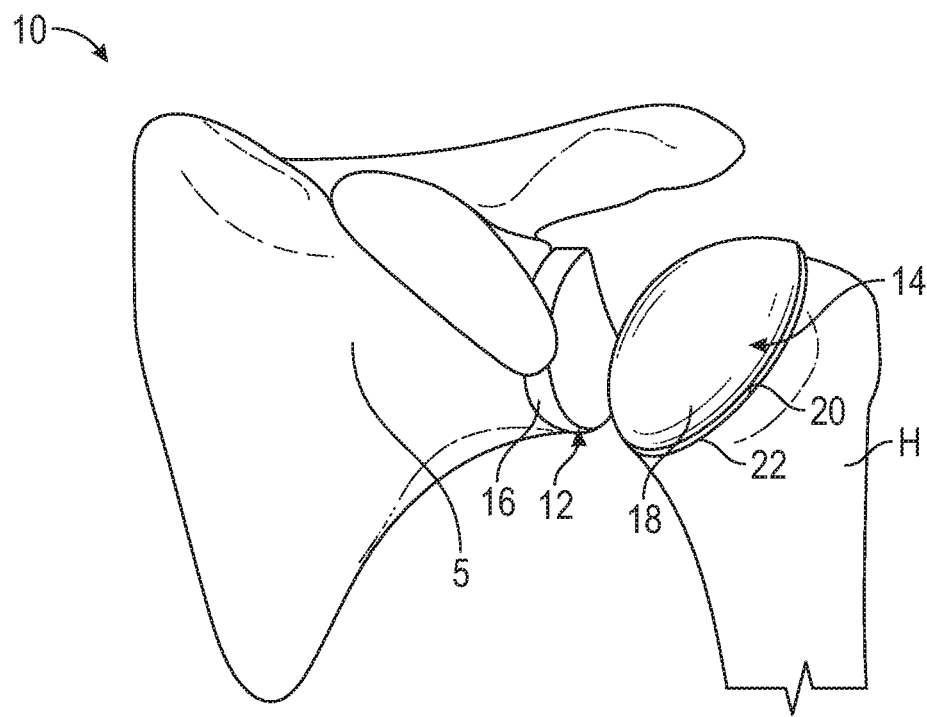
FIG. 1 is a front perspective view of a total shoulder arthroplasty system in which a humerus bone includes a humeral head prosthetic device system.

FIG. 1 is a front perspective view of total shoulder arthroplasty system 10 comprising implanted prosthetic glenoid 12 and implanted humeral head prosthetic device system 14. Prosthetic glenoid 12 can include glenoid 16 and humeral head prosthetic device system 14 can include humeral head 18. Glenoid 16 can be secured to scapula bone S using any suitable means, such as a center post and a plurality of peripheral posts. Humeral head 18 can be secured to humerus bone H via coupling device 24 that connects to a humeral adapter 28 coupled to humeral stem 30, as shown in FIG. 2.

Scapula bone S and humerus bone H are typically reamed, resected or otherwise prepared to receive glenoid 16 and humeral head 18. As can be seen, humeral head 18 can be mounted to humerus bone H such that the perimeter 20 of humeral head 18 can be substantially aligned with edge 22 of humerus bone H. It can be desirable for humeral head 18 to be properly centered on humerus bone H to achieve correct anatomic operation, for example, so that humeral head 18 can smoothly rotate against glenoid 16. As such, the size of humeral head 18 can be selected so that the diameter of perimeter 20 substantially matches that of edge 22. It is not, however, always possible for humeral head 18 to be optimally aligned with edge 22 upon implantation. For example, humeral stem 30 and humeral adapter 28 (FIG. 2) are not always implanted into humerus bone H such that the neck (e.g., neck 98A of FIG. 4) for receiving humeral head 18 is centered to align with glenoid 16. As such, the present disclosure provides a system and method for sizing, trialing and aligning humeral head 18 with humerus bone H.

Figure 2:
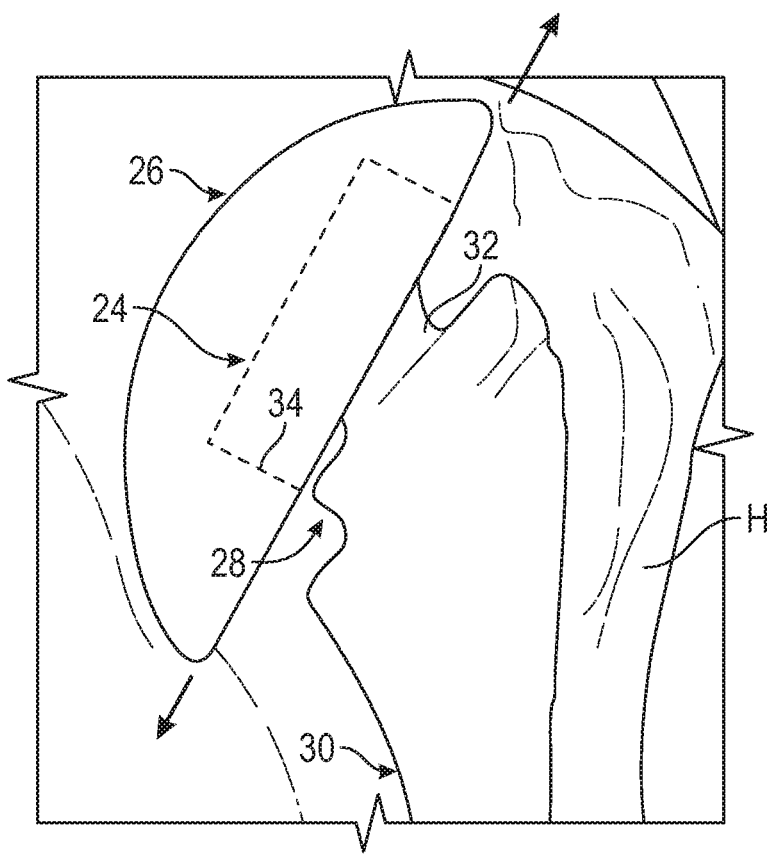
FIG. 2 is a schematic illustration of the humeral head prosthetic device system of FIG. 1 implanted in a humerus bone and showing a coupling device connecting a prosthetic head with a humeral adapter and a humeral stem.

FIG. 2 is a schematic illustration of a humeral head prosthetic device system, such as system 10 of FIG. 1, implanted in humerus bone H and showing coupling device 24 connecting prosthetic head 26 with humeral adapter 28 and humeral stem 30. Humerus bone H can be reamed to accept humeral stem 30 in any suitable manner. Humeral stem 30 can include a socket for receiving humeral adapter 28. Humeral adapter 28 can include neck 32 for connecting to coupling device 24. Coupling device 24 can be inserted into prosthetic head 26 at socket 34. Prosthetic head 26 can comprise or be substituted for humeral head 18 of FIG. 1.

The translational and rotational position of prosthetic head 26 relative to stem 30 can be changed to help ensure that prosthetic head 26 aligns with the humerus bone H and with the glenoid of a scapula. In one example, coupling device 24 can have a socket for neck 32 that is offset from the center of coupling device 24. In another example, socket 34 in prosthetic head 26 can be offset from the center of prosthetic head 26. Additionally, combinations of offset components can be used, as is discussed with reference to FIG. 4. Trialing device 36 (FIGS. 3A and 3B) can be used to select a prosthetic head 26 and a compatible coupling device 24. In another embodiment, coupling device 24 can comprise trialing device 36.

Figure 3A:
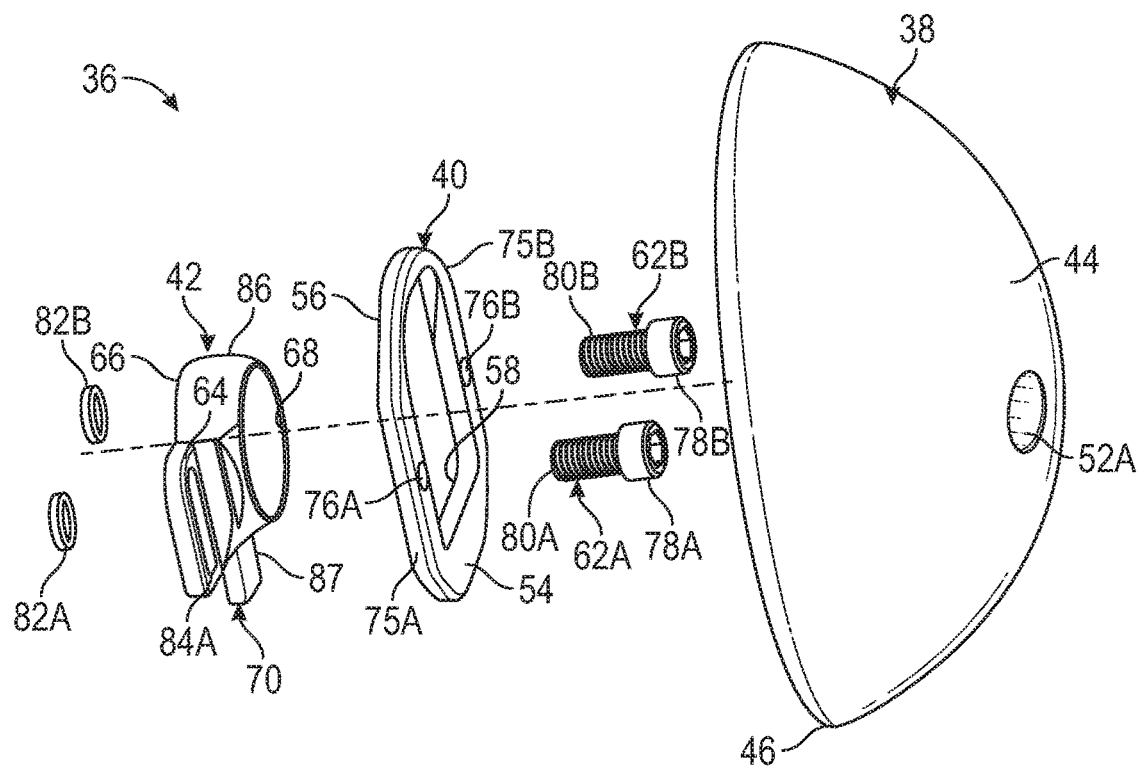
FIGS. 3A and 3B are lateral and medial exploded views of a trialing device for use as or selection of the coupling device of FIG. 2 showing a trialing head, a mounting plate and an adapter coupling plate.
Figure 3B:
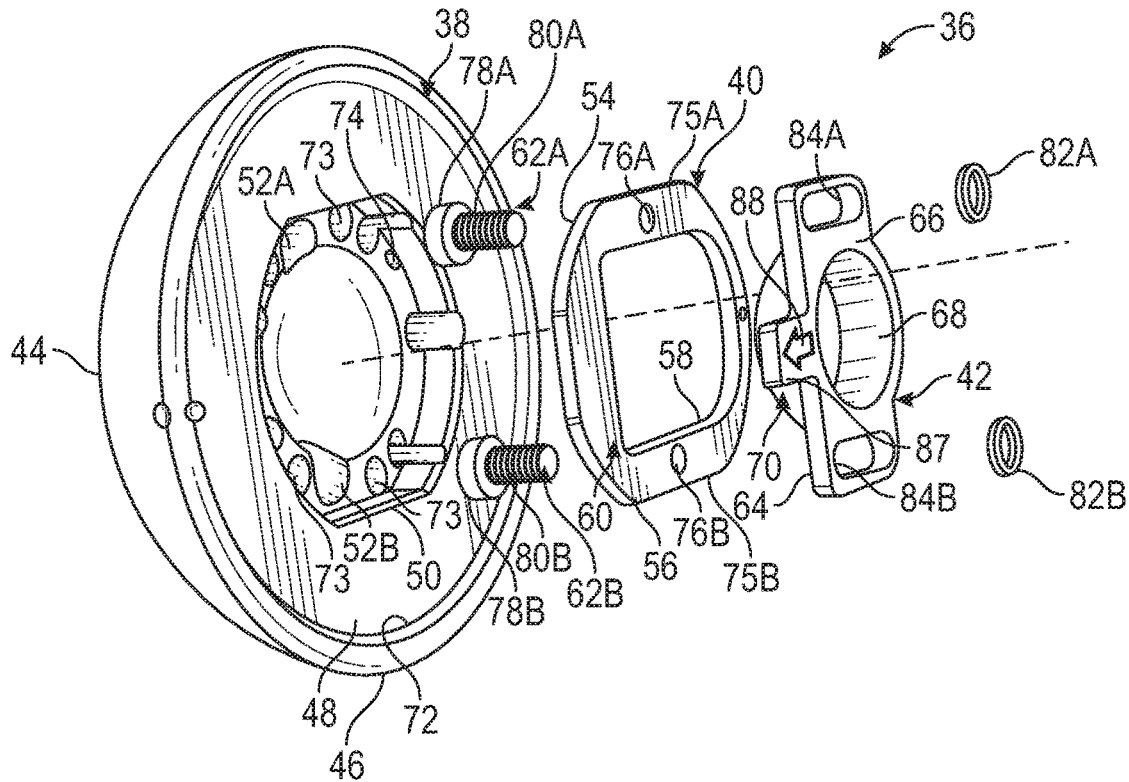

FIGS. 3A and 3B are lateral and medial exploded views of trialing device 36 for use as, or selection of, coupling device 24 of FIG. 2, which shows trialing head 38, mounting plate 40 and adapter coupling plate 42. Trialing head 38 can comprise curved articulating surface 44, edge perimeter 46, interior surface 48, socket 50 and access openings 52A and 52B. Mounting plate 40 can comprise first major surface 54, second major surface 56, adapter accommodation hole 58 and indicia 60. Slide posts 62A and 62B can extend from and/or through mounting plate 40. Adapter coupling plate 42 can comprise third major surface 64, fourth major surface 66, adapter coupling hole 68 and indicator 70.

Figure 4:
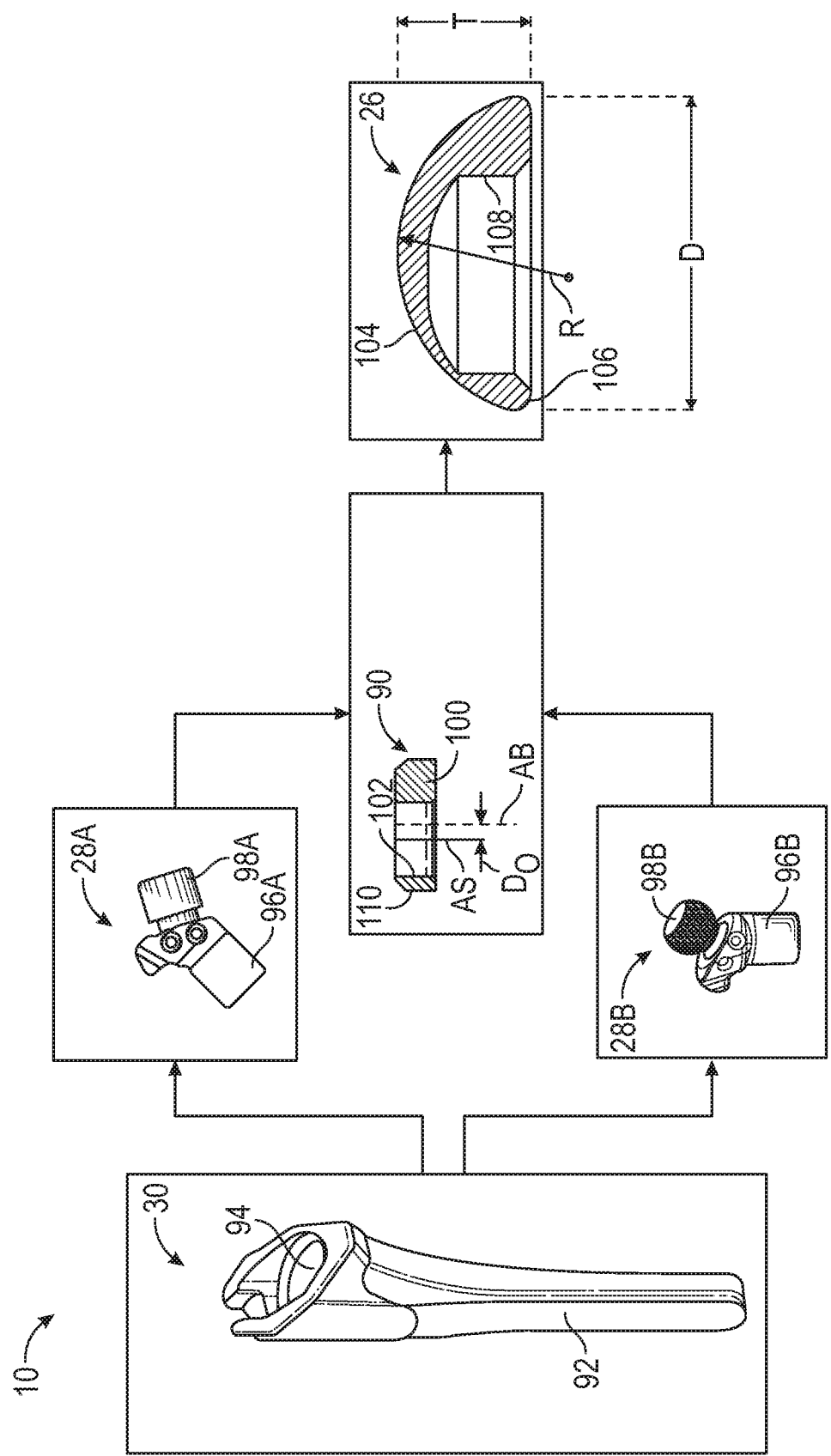
FIG. 4 is a flow chart of the humeral head prosthetic device system of FIG. 2 showing a conversion ring for use as the coupling device and connecting the prosthetic head with the humeral adapter and the humeral stem.

Curved articulating surface 44 can be shaped to approximate the shape of a natural or anatomic humeral head. Curved articulating surface 44 can be smooth and can have a center that substantially aligns with the center of trialing head 38, which can comprise the center of edge perimeter 46, which can be circular. Interior surface 48 can be flat and can be configured to face towards or abut a planar resection of humerus bone H. Trialing head 38 can include recess 72 that can allow edge perimeter 46 to extend out past socket 50 to envelop or partially cover portions of humeral adapters 28A and 28B (FIG. 4).

Mounting plate 40 can be inserted into socket 50 such that first major surface 54 faces toward access openings 52A and 52B and can thus be disposed inside of trialing head 38. In an example, socket 50 can include magnets 73 that assist with retaining mounting plate 40 within trialing head 38. First major surface 54 can be flat to abut against surface 74 inside socket 50. Socket 50 can be sized and configured to provide a frictional fit with the outer perimeter of mounting plate 40 that joins first major surface 54 and second major surface 56. The outer perimeter of mounting plate 40 can include flats 75A and 75B that can engage with corresponding flat surfaces of socket 50 to prevent rotation.

Slide posts 62A and 62B can extend through mounting plate 40 so as to project therefrom. In particular, mounting plate 40 can include post holes 76A and 76B that can allow slide posts 62A and 62B to extend through mounting plate 40. Slide posts 62A and 62B can include heads 78A and 78B, shafts 80A and 80B and stops 82A and 82B, respectively. Post holes 76A and 76B can be threaded to mate with corresponding threading on shafts 80A and 80B. Stops 82A and 82B can be nuts or washers and/or can be affixed to shafts 80A and 80B, respectively, in a stationary manner, such as by welding. As such, for example, a driver instrument, e.g., a screw driver or driver instrument 118 of FIG. 8, can engage a drive socket in head 78A to rotate shaft 80A and to cause slide post 62A to move relative to post hole 76A via the threaded engagement. Thus, shaft 80A can be advanced into post hole 76A to move stop 82A away from second major surface 56 or can be retreated from post hole 76B to move stop 82A toward second surface 56. Slide post 62B can operate in a similar manner. Thus, with adapter coupling plate 42 positioned against mounting plate 40, stops 82A and 82B can be used to pull adapter coupling plate 42 into compression with mounting plate 40 to thereby immobilize adapter coupling plate 42 relative to mounting plate 40.

Third major surface 64 of adapter coupling plate 42 can be positioned against second major surface 56 of mounting plate 40. Adapter coupling plate 42 can include slots 84A and 84B that can align with post holes 76A and 76B, respectively. Slots 84A and 84B each have a major axis and a minor axis. The minor axes can be slightly longer than the width of slide posts 62A and 62B, thereby limiting side-to-side (relative to the orientation of FIG. 3A) movement of adapter coupling plate 42, and can be less than the width of stops 62A and 62B, thereby preventing slide posts 62A and 62B from withdrawing from slots 84A and 84B. The major axes can be longer than the width of slide posts 62A and 62B, thereby permitting up-and-down (relative to the orientation of FIG. 3A) movement of adapter coupling plate 42.

Adapter coupling hole 68 can align with adapter accommodation hole 58. Adapter coupling hole 68 can be sized and configured to mate with neck 98A or neck 98B of humeral adapter 28A and humeral adapter 28B, respectively, of FIG. 4. Adapter coupling hole 68 can be typically round in shape and can form wall 86 to receive the desired neck. In one example wall 86 can be flat and straight such that coupling hole 68 is cylindrical. In another example, wall 86 can be flat and angled such that coupling hole 68 is conical in shape. In another example, wall 86 can be arcuate such that coupling hole 68 is hemi-spherical in shape. Adapter accommodation hole 58 can be larger than adapter coupling hole 68. As such, a neck extending through adapter coupling hole 68 and into adapter accommodation hole 58 can be moved around within the area of adapter accommodation hole 58 as adapter coupling plate 42 slides against mounting plate 40.

Figure 6:
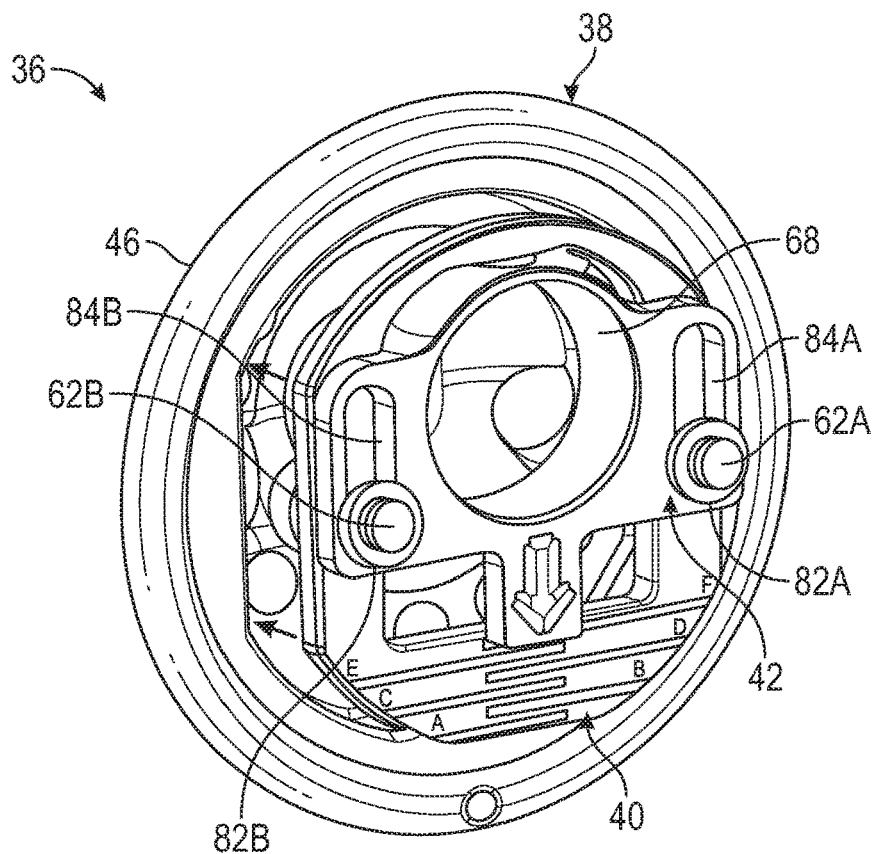
FIG. 6 is a perspective view of the trialing device of FIGS. 3A and 3B assembled with the trialing head and showing the adapter coupling plate connected to the mounting plate via a pair of slide posts.

When trialing device 36 is assembled, adapter coupling plate 42 can slide against mounting plate 40 to change the position of trialing head 38 relative to coupling hole 68. Adapter coupling plate 42 can slide along slide posts 62A and 62B at slots 84A and 84B to change the position of the center of curved articulating surface 44 relative to the center of coupling hole 68, thereby changing the offset of trialing device 36. In the orientation shown, the position of coupling hole 68 is changed in the up-and-down direction (relative to the orientation of FIG. 3A). Trialing device 36 can be rotated about the neck that is inserted in coupling hole 68 to allow the position of coupling hole 68 to be changed in the side-to-side direction (relative to the orientation of FIG. 3A). The relative position between adapter coupling plate 42 and mounting plate 40 can be marked, identified or shown using indicia 60 and indicator 70. In particular, indicator 70 can be any feature or marking that provides a constant frame of reference on adapter coupling plate 42 and that overlaps or otherwise interacts with indicia 60. In the example of FIGS. 3A and 3B, indicator 70 comprises an edge of flange 87 on adapter coupling plate 42 that overlaps with hash marks defining indicia 60. Each of the hash marks can correspond to an offset size of a prosthetic humeral head. For example, as can be seen in FIG. 6, size A can correspond to a zero offset where the center of coupling hole 68 aligns with the center of curved articulating surface 44, with sizes B-F indicating progressively larger offsets. Indicator 70 can include marker 88 that prompts a user where to look to take the size reading. In the example shown, marker 88 comprises an arrow pointing to the edge of flange 87 that overlaps with indicia 60.

FIG. 4 shows an installation relationship of humeral head prosthetic device system 10 of FIGS. 1 and 2 showing conversion ring 90 for use as coupling device 24 and connecting prosthetic head 26 with humeral adapters 28A or 28B and humeral stem 30.

Humeral stem 30 can comprise shank 92 and socket 94. Humeral adapter 28A can comprise post 96A and neck 98A and can be configured as a fixed angle adapter. Humeral adapter 28B can comprise post 96B and neck 98B and can be configured as a variable angle adapter. Conversion ring 90 can comprise body 100 having neck bore 102. Prosthetic head 26 can comprise outer surface 104, inner surface 106 and socket 108.

Humeral stem 30 can be configured in a conventional manner to be implanted into cancellous bone of a long bone. In one example, humeral stem 30 is configured to be implanted into a humerus bone wherein the humeral head has been resected. However, the systems and methods of the present disclosure are readily applicable to and adapted for use with other bones, such as femurs. Shank 92 can be inserted into the cancellous bone to anchor stem 30 within the bone in a stationary fashion. Socket 94 can remain exposed to receive one of adapters 28A and 28B, which are configured to mate with conversion ring 90.

Posts 96A and 96B can be configured similar to each other so as to mate with socket 94 of humeral stem 30 such that adapters 28A and 28B comprise modular alternatives for use with humeral stem 30. In an example, posts 96A and 96B have an oblong shape that mates with a similarly oblong shaped socket 94. The mating oblong shapes prevent rotation of posts 96A and 96B in stem 30. Necks 98A and 98B extend from posts 96A and 96B, respectively, at fixed angles in order to initially set prosthetic head 26 at a fixed angle relative to stem 30. For example, an axis extending along the center of post 96A is at a fixed angle relative to an axis extending along the center of neck 98A, thereby locating the axis of neck 98A in a fixed relationship to an axis extending along the center of shank 92. Humeral adapter 28B can be configured in a similar manner. In other examples, humeral stem 30 can be made monolithically with either of adapters 28A and 28B so as to form a one-piece humeral stem component. In other examples, a one-piece humeral stem component or an adapter can include a Morse taper in place of necks 98A and 98B.

Neck 98A can comprise a fixed angle neck such that the angle between prosthetic head 26 and shank 92 cannot be adjusted once stem 30, adapter 28A and conversion ring 90 are assembled. As such, the wall surfaces of neck 98A can be flat to engage flat surfaces of neck bore 102 of conversion ring 90.

Neck 98B can comprise a variable angle neck such that the angle between prosthetic head 26 and shank 92 can be slightly adjusted once stem 30, adapter 28B and conversion ring 90 are assembled. As such, the wall surfaces of neck 98B can be curved to engage curved surfaces of neck bore 102 of an embodiment of conversion ring 90 different from the one shown in FIG. 4.

Conversion ring 90 comprises a component that allows prosthetic head 26 to mate with adapters 28A and 28B. Side surfaces 110 of body 100 can be shaped to match the shape of socket 108 of prosthetic head 26. Socket 108 and side surfaces 110 can have an asymmetric shape to prevent rotation between conversion ring 90 and prosthetic head 26. As shown in FIG. 4, a central axis $A_B$ of body 100 can be offset from a central axis As 102 of socket 102. Thus, different conversion rings 90 can be configured with different offset distances $D_O$ to position prosthetic head 26 in different locations relative to stem 30 for different situations, such as depending on the implantation of stem 30 into the cancellous bone and the particular humeral head anatomy and mating glenoid anatomy or prosthetic. Trialing device 36 can be used to determine the desired conversion ring 90 to be used in a particular implant system. Trialing device 36 can alternatively be used in place of conversion ring 90 due to the ability of adapter coupling plate 42 being able to equivalently shift the location of axis As relative to axis $A_B$. Different prosthetic heads can be coupled to conversion ring 90 to match or closely mimic the anatomy of a patient.

As discussed, socket 108 of prosthetic head 26 is sized and shaped to fit with side surfaces 110 of conversion ring 90. Socket 108 can be deep enough to receive the entire thickness of conversion ring 90 such that inner surface 106 can be positioned in close proximity to a resected humeral surface. Prosthetic head 26 can include outer surface 104 that can be curved or arcuate to mate with an anatomic or prosthetic glenoid cavity. Outer surface 104 defines the geometry of prosthetic head 26. For example, prosthetic head 26 can have, in different embodiments, different thicknesses T, different diameters D and different radii R. Thus, a surgeon can intraoperatively select from among a plurality of different sized prosthetic heads 26 to find a prosthetic head that closely matches the anatomy of a particular patient.

Figure 5:
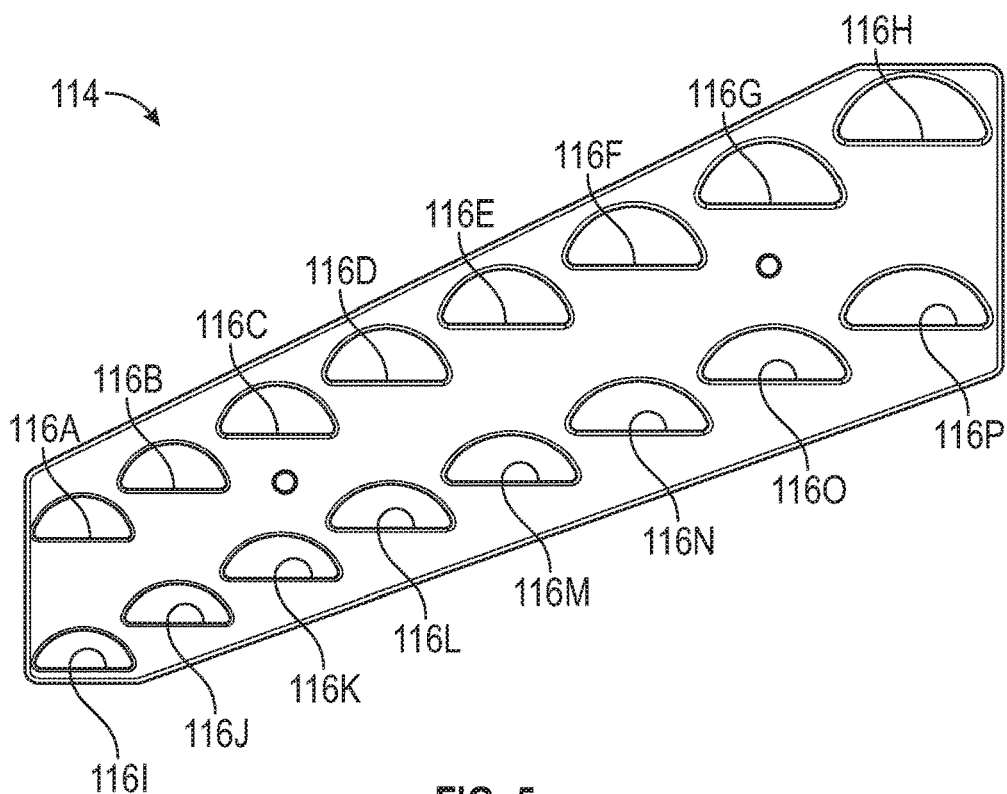
FIG. 5 is a front view of a humeral head template used to initially size a humeral head trial or prosthetic.

FIG. 5 is a front view of humeral head template 114 used to initially size a humeral head trial or prosthetic, such as the exemplary humeral head 18 of FIG. 1, prosthetic humeral head 26 of FIG. 2 or trialing humeral head 38 of FIGS. 3A and 3B. Template 114 includes slots 116A-116P that have different geometries, such as thicknesses, diameters and radii. After a humeral head has been resected to remove a hemi-spherical-like shaped portion of the bone, the resected bone portion is positioned within different slots 116A-116P in order to find the initial size of a head component that can be implanted into a that particular patient. For example, a surgeon can select which of slots 116A-116P the resected humeral head matches closest. That particular slot can, for example, indicate to the surgeon the thickness T, diameter D and radius R of a prosthetic head 26 that can be used to closely match the anatomy of the patient.

FIG. 6 is a perspective view of trialing device 36 of FIGS. 3A and 3B assembled with trialing head 38 and showing adapter coupling plate 42 connected to mounting plate 40 via slide posts 62A and 62B. Trialing head 38 can be selected to match the geometry of the resected humeral head determined using template 114. Mounting plate 40 can be inserted into trialing head 38 to secure components of trialing device 36 thereto. For example, the outer perimeter of mounting plate 40 can be inserted into socket 50 of trialing head 38 via an interference or friction fit. Slide posts 62A and 62B can be retracted further out of post holes 76A and 76B to permit adapter coupling plate 42 to slide relative to mounting plate 40 in slots 84A and 84B, respectively. Next, a humeral adapter, such as one of adapters 28A and 28B of FIG. 4, can be inserted into coupling hole 68 in adapter coupling plate 42. With slide posts 62A and 62B loosened such that stops 82A and 82B do not pull coupling plate 42 into compression with mounting plate 40, coupling plate 42 can be slid against mounting plate 40 to move edge perimeter 46 relative to resected humeral bone, as shown in FIG. 7.

Figure 7:
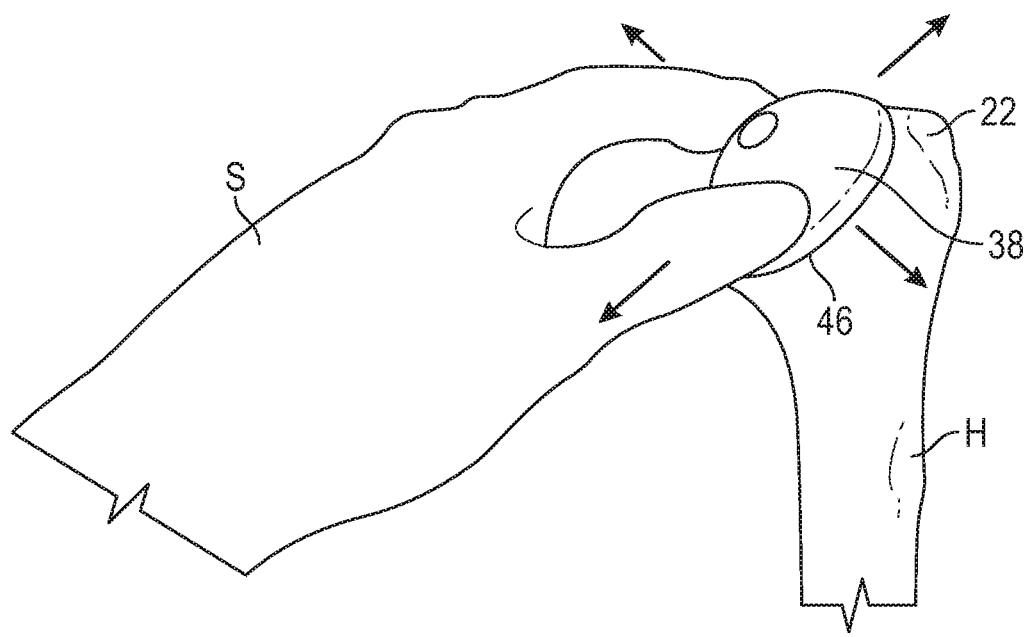
FIG. 7 is a schematic perspective view of the trialing head of FIG. 6 coupled to a humeral adapter implanted into a humerus bone illustrating multiple degrees of freedom of movement.

FIG. 7 is a perspective view of trialing head 38 of FIG. 6 coupled to a humeral adapter (not shown for clarity) implanted into humerus bone H and illustrates multiple degrees of freedom of movement. Humeral stem 30 can be implanted into humerus bone H in a conventional manner. Humeral adapter 28A or 28B can be connected to humeral stem 30, as previously described. Adapters 28A or 28B can be used to couple trialing head 38 to trialing device 36. For example, post 96A of adapter 28A can be inserted into humeral stem 30 and neck 98A of adapter 28A can be inserted into coupling hole 68 of adapter coupling plate 42. Surgeon S can move trialing head 38 in multiple directions by sliding of plates 40 and 42 relative to each other and by rotating adapter coupling plate 42 about an axis of neck 98A. Thus, edge perimeter 46 of trialing head 38 can be moved relative to edge 22 of humerus bone H to position trialing head 38 in the proper position. For example, the center of trialing head 38 can be positioned in the center of the resected surface of humerus bone H so that edge perimeter 46 is concentric with edge 22.

Figure 8:
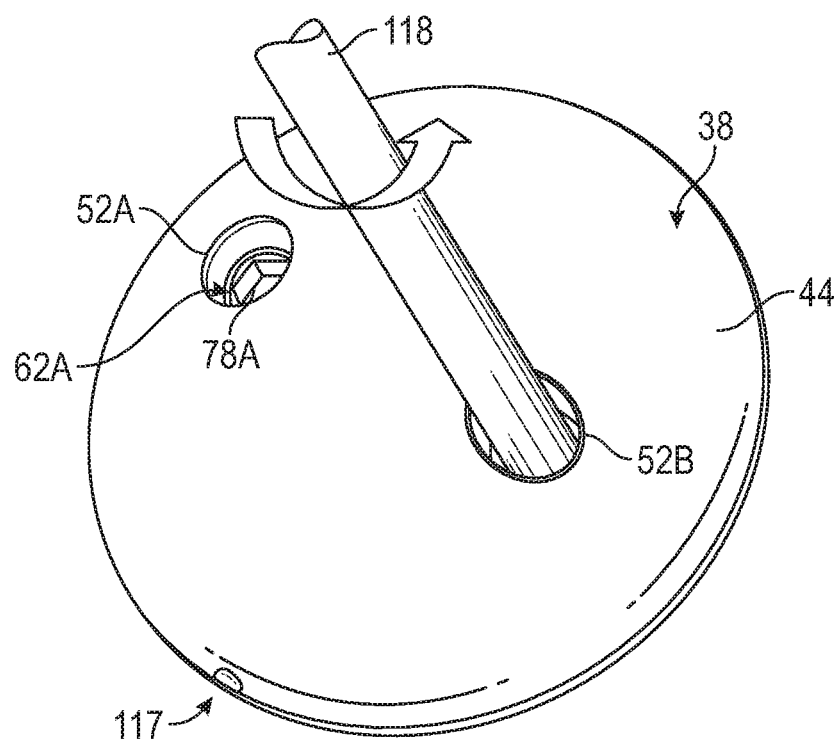
FIG. 8 is a perspective view of an exterior of the trialing head of FIG. 7 showing a driver instrument adjusting one of the slide posts.
Figure 9:
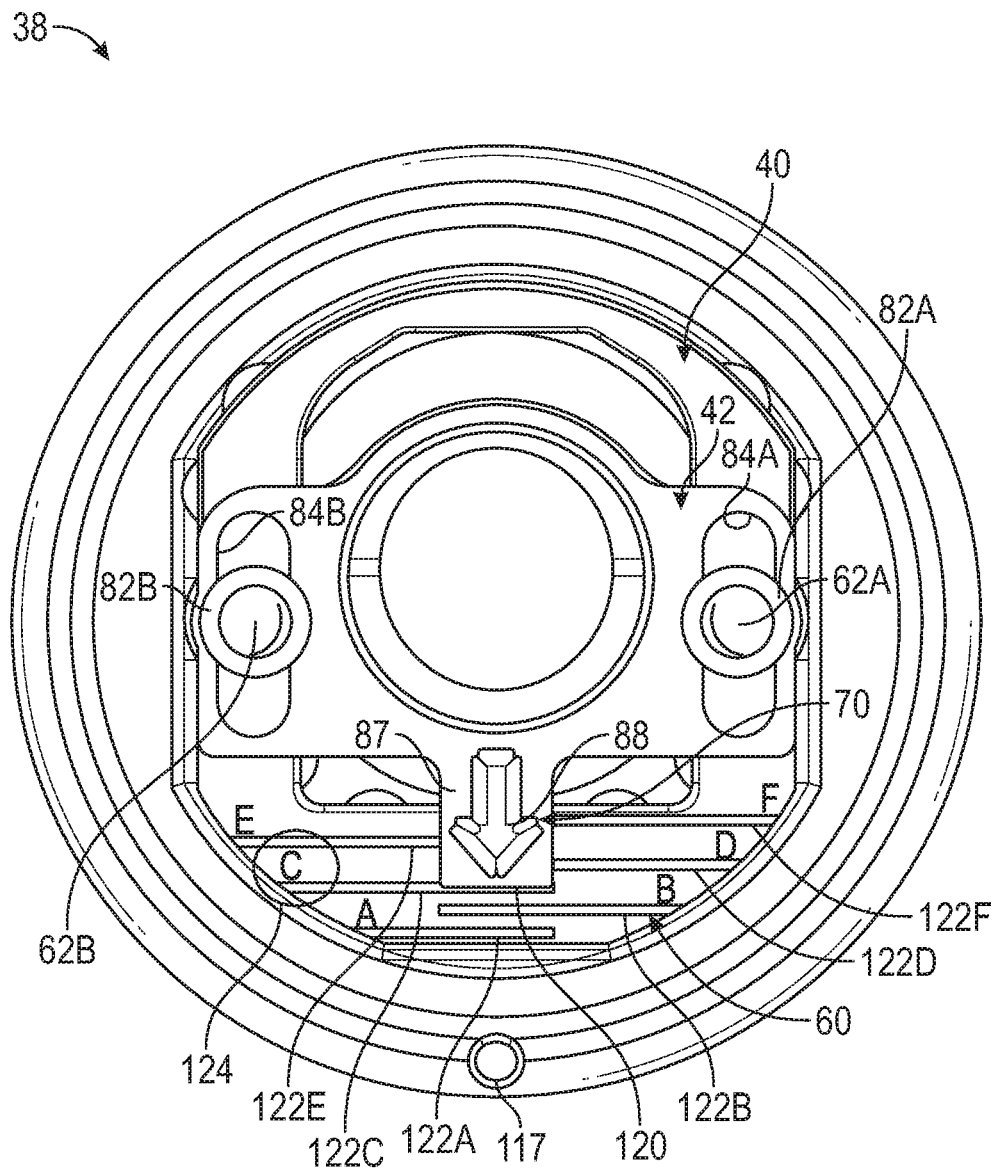
FIG. 9 is an interior side view of the trialing device of FIGS. 6-8 after adjustment showing an indicator aligning with sizing indicia.

The position of trialing head 38 relative to humerus bone H can be marked on humerus bone H using an appropriate marker. For example, as shown in FIG. 8, the location of marker 117 on trialing head 38 can be marked on humerus bone H using a surgical marker or a electrocautery, e.g. a Bovie. As shown in FIG. 9, marker 117 can extend through trialing head 38, or have a corresponding mark on the opposite side, so as to be visible to a surgeon from both sides of trialing head 38. Marker 117 can allow the surgeon to reassemble trialing head 38 to trialing device 36 or reposition trialing head 38 on trialing device 36 into the same position on the marked-up humerus bone H if for some reason trialing head 38 had to be removed or trialing device 36 needed to be repositioned.

FIG. 8 is a perspective view of an exterior of trialing head 38 of FIG. 7 showing slide post 62A and driver instrument 118 inserted into articulating surface 44 to adjust slide post 62B. Trialing head 38 includes access openings 52A and 52B that permit driver instrument 118 to enter the interior region of trialing head 38 to access slide posts 62A and 62B. Heads 78A and 78B of slide posts 62A and 62B can be positioned within trialing head 38 via mounting plate 40 to align with access openings 52A and 52B. Slide posts 62A and 62B can be rotated to tighten trialing device 36 so that the position of trialing head 38 relative to coupling plate 42 does not change. For example, with reference to FIG. 6, slide posts 62A and 62B can be tightened such that stops 82A and 82B pull coupling plate 42 into compression with mounting plate 40, preventing coupling plate 42 from sliding against mounting plate 40. Although FIG. 8 shows trialing device 36 having a pair of slide posts 62A and 62B, other examples of trialing devices of the present application can be immobilized using only a single slide post. In another embodiment, coupling plate 42 and mounting plate 40 can be configured to slide relative to each other in other arrangements in which slide posts 62A and 62B are not used. For example, coupling plate 42 can be configured to slide directly within a slot in mounting plate 40, and a separate fastener can be used to lock the relative positions of the plate.

In another example of the trialing devices of the present application, coupling plate 42 can be immobilized relative to mounting plate 40 via a deformable body that can be deformed via slide posts 62A and 62B. For example, stops 82A and 82B could be replaced with deformable sleeves that can slide within slots 84A and 84B respectively. Slide posts 62A and 62B can be sized to be threaded or inserted into the deformable sleeves to radially expand the deformable sleeves to push them against slots 84A and 84B, thereby immobilizing coupling plate 42. In other examples, other types of deformable bodies may be activated by one or more slide posts to frictionally engage coupling plate 42 and mounting plate 40 with each other.

FIG. 9 is an interior side view of trialing device 38 of FIGS. 6-8 after adjustment, where an edge of flange 87 aligns with sizing indicia 60. In particular, edge 120 of flange 87 can align with hash marks 122A-122F to indicate the size of prosthetic to be used with the patient. As identified by callout 124 in FIG. 9, edge 120 of flange 87 aligns with hash mark 122C, indicating that a size C prosthetic humeral head can be used. As mentioned, size C can be offset from a zero offset position indicated by hash mark 122A. In other examples, more or fewer sizes/hashmarks can be indicated on mounting plate 40. In other examples, other types of sizing indicia or indicators can be used. For example, marks along the edges of coupling plate 42 along slots 84A and 84B can be used to align with hash marks along the sides of mounting plate 40.

The present subject matter can help provide a solution to various problems associated with the trialing of a humeral head by providing trialing device 36, or a similar device such as those discussed below with reference to FIGS. 10-20F, that can be used to couple humeral stem 30 or humeral adapters 28A and 28B with multiple humeral head trials, such as such as humeral head 18 of FIG. 1, prosthetic head 26 of FIG. 2 or trialing head 38 of FIGS. 3A and 3B. The trialing devices described herein can be locked in place without removing the humeral head trial from the anatomy, such as by rotating slide posts 62A and 62B from the exterior of trialing head 38 for trialing device 36 to ensure accurate readings are taken from indicator 70 and sizing indicia 60 and a proper head size is selected. The trialing devices described herein can be easily assembled and disassembled, cleaned and reused, thereby minimizing the number of components and instruments that must be maintained in inventory.

Figure 10:
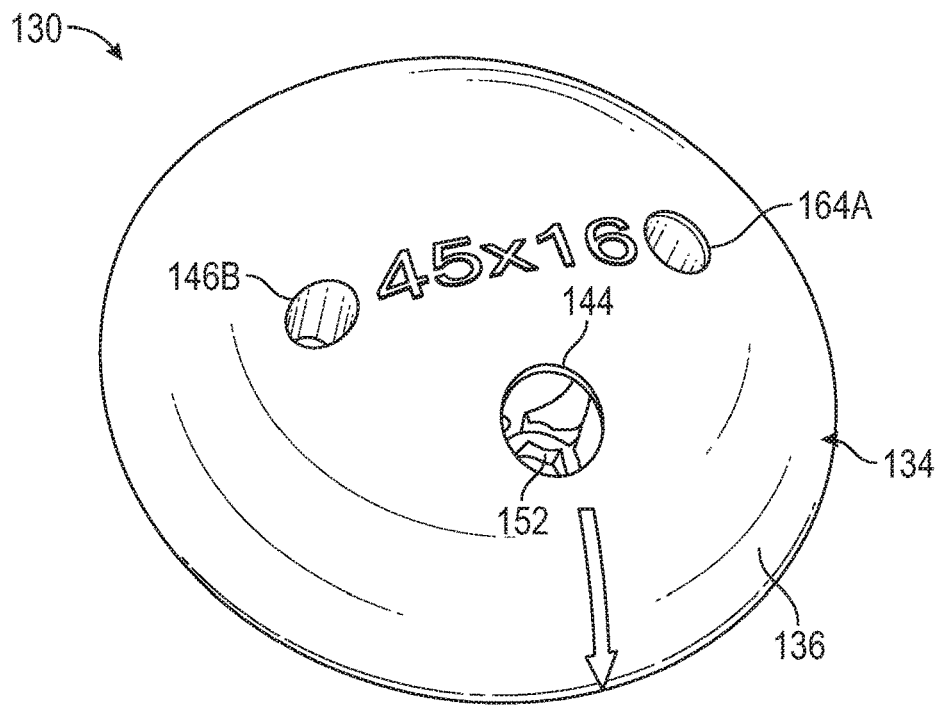
FIG. 10 is a perspective view of another embodiment of a humeral head trialing device for use with the humeral head prosthetic device system of FIG. 4 wherein a slide plate includes slots for receiving rails of a bushing.
Figure 11:
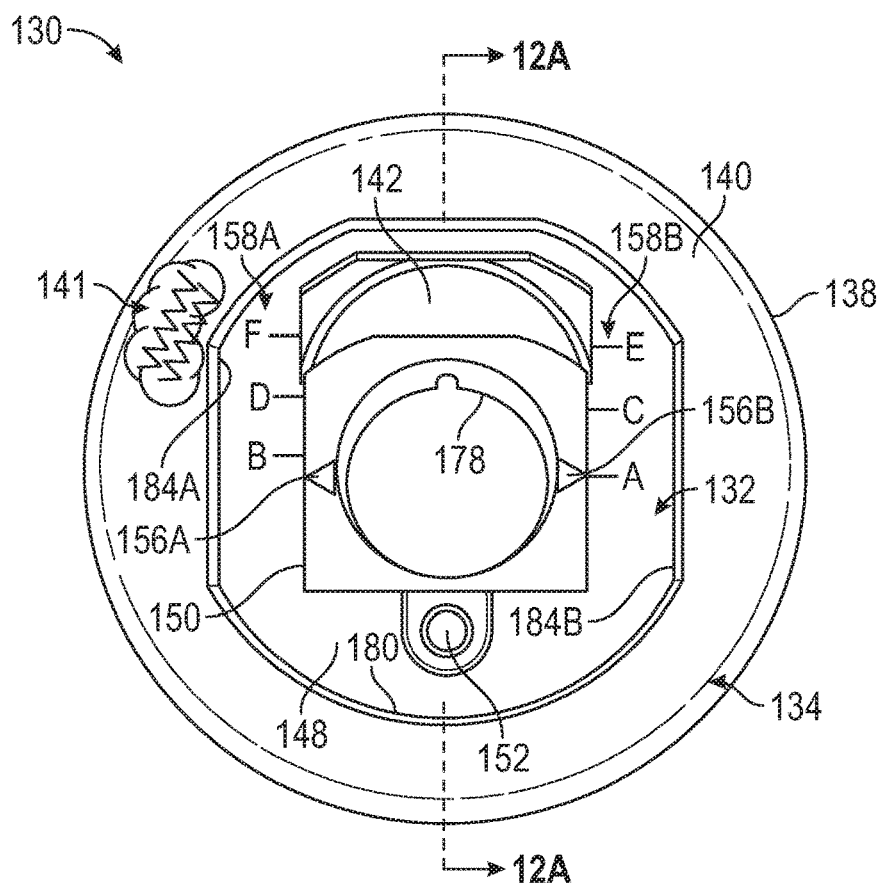
FIG. 11 is a bottom plan view of the humeral head trialing device of FIG. 10 showing an embodiment of an offset slide device within a trialing head.

FIG. 10 is a perspective view of humeral head trialing device 130 for use with humeral head prosthetic device system 10 of FIG. 4. FIG. 11 is a bottom plan view of humeral head trialing device 130 of FIG. 10 showing offset slide device 132 within trialing head 134. Humeral head trialing device 130 is similar to humeral head trialing device 36 of FIGS. 3A and 3B except, for example, humeral head trialing device 130 includes only a single fastener for locking offset slide device 132 and humeral head trialing device 130 slides on rails rather than posts.

Trialing head 134 can comprise curved articulating surface 136, edge perimeter 138, interior surface 140, socket 142, access opening 144 and sockets 146A and 146B. Offset slide device 132 can include slide plate 148 and bushing 150. Slide plate 148 and bushing 150 can be coupled together using fastener 152. Slide plate 148 and bushing 150 can operate in a similar fashion as mounting plate 40 and adapter coupling plate 42 of humeral head trialing device 36, respectively. However, rather than adapter coupling plate 42 sliding against mounting plate 40 in an abutting relationship, bushing 150 can include rails that are captured within channels of slide plate 148.

As shown in FIG. 11, slide plate 148 can be inserted into recess 180 of trialing head 134 and can be held in place by frictional interaction between slide plate 148 and trialing head 134 at recess 180. Fastener 152 can be extended into access opening 144 to engage fastener bore 164 (FIG. 12A) in slide plate 148 to prevent slide plate 148 from separating from trialing head 134. Bushing 150 can slide between trialing head 134 and slide plate 148 such that indicators 156A and 156B can align with size indicia 158A and 158B on slide plate 148. Fastener 152 can be adjusted to pull slide plate 148 toward trialing head 134 to immobilize bushing 150.

Figure 12A:
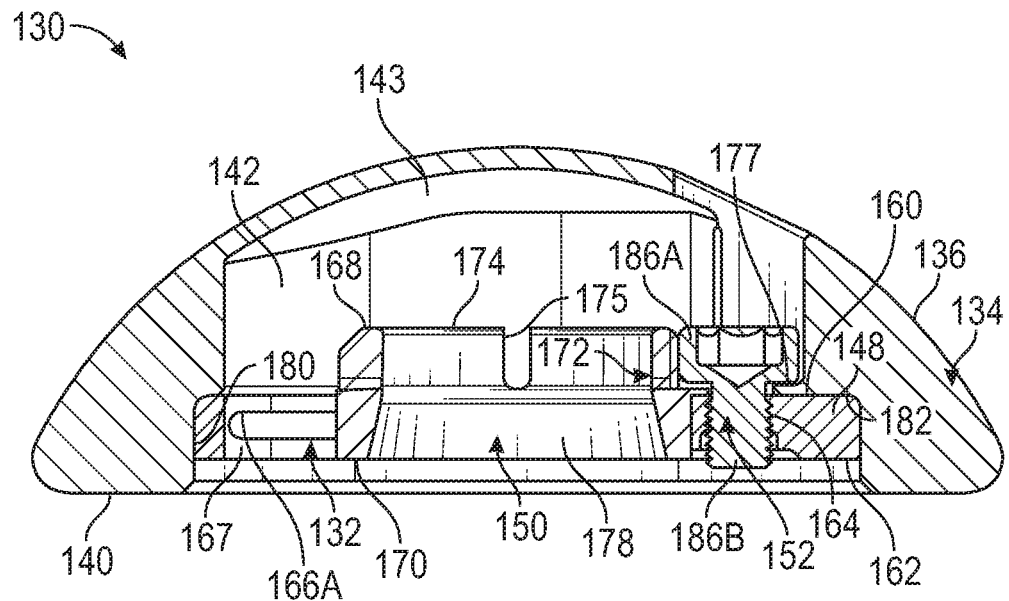
FIG. 12A is a cross-sectional view of the humeral head trialing device of FIG. 11 taken along a center of the device to show the offset slide device having a trialing head, a slide plate, a bushing and a set screw.
Figure 12B:
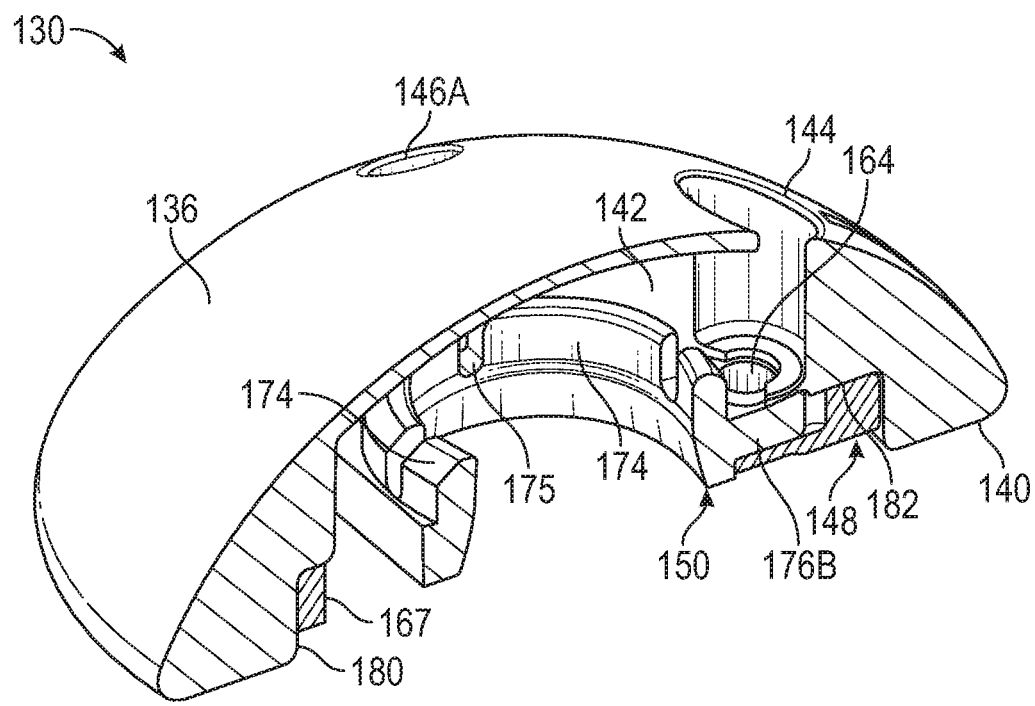
FIG. 12B is a perspective cross-sectional view of the humeral head trialing device of FIG. 11 taken offset from a center of the device to show a bushing rail.

FIG. 12A is a cross-sectional view of humeral head trialing device 130 of FIG. 11 showing offset slide device 132 having trialing head 134, slide plate 148, bushing 150 and fastener 152. FIG. 12B is a perspective cross-sectional view of humeral head trialing device 130 of FIG. 11 taken offset from a center of the device to show rail 176B.

Slide plate 148 can comprise fifth major surface 160, sixth major surface 162, fastener hole 164, first slot 166A and second slot 166B (not visible in FIGS. 12A and 12B), and aperture 167.

Bushing 150 can comprise first end surface 168, second end surface 170, adapter coupling hole 172, flanges 174, rails 176A (not visible in FIGS. 12A and 12B) and 176B and ledge 177. End surfaces 168 and 170 can be considered the major surfaces of bushing 150. Bushing 150 can comprise a rectilinear body having four sides bounded by first end surface 168 and second end surface 170. Rails 176A and 176B can extend from opposite sides of the rectilinear body to engage slots 166A and 166B. Flanges 174 can extend from first end surface 168 to surround socket 178, which can extend through the rectilinear body from second end surface 170 through to first end surface 168. Flanges 174 can be separated by scallops or cut-outs 175 in bushing 150. Flanges 174 can comprise resilient bodies that are separated by cut-outs 175 to facilitate flexion to increase frictional engagement with neck 98A or 98B.

Curved articulating surface 136 can be shaped to approximate the shape of a natural or anatomic humeral head. Curved articulating surface 136 can be smooth and can have a center that substantially aligns with the center of trialing head 134, which can comprise the center of edge perimeter 138, which can be circular. Interior surface 140 can be flat and can be configured to face towards or abut a planar resection of humerus bone H. Interior surface 140 can be smooth or textured. Texturing 141 of interior surface 140 can facilitate locking of trialing head 134 into place via friction with the humerus bone H, thereby preventing trialing head 134 from migrating out of position once aligned. The texturing 141 can comprise knurling, pointed projections, spikes, pyramids and the like. Trialing head 134 can include recess 180 that can engage slide plate 148 in order to allow edge perimeter 138 to extend out past socket 142 and slide plate 148 to envelop or partially cover portions of humeral adapters 28A and 28B (FIG. 4).

Slide plate 148 can be inserted into socket 142 at recess 180 such that fifth major surface 160 faces toward access opening 144 and can thus be disposed inside of trialing head 134. In an example, socket 142 can include magnets (e.g., magnets 73 of FIG. 3B or magnets 280A and 280B of FIG. 19) that assist with retaining slide plate 148 within trialing head 134. Fifth major surface 160 can be flat to abut against surface 182 inside socket 142. Recess 180 can be sized and configured to provide a frictional fit with the outer perimeter of slide plate 148 that joins fifth major surface 160 and sixth major surface 162. The outer perimeter of slide plate 148 can include flats 184A and 184B that can engage with corresponding flat surfaces of recess 180 to prevent rotation.

Socket 178 can be sized and configured to mate with neck 98A or neck 98B of humeral adapter 28A or humeral adapter 28B, respectively, of FIG. 4. Socket 178 can be typically round in shape and can form a wall to receive the desired neck. In one example the wall can be flat and straight such that socket 178 is cylindrical. In another example, the wall can be flat and angled such that socket 178 is conical in shape. In another example, the wall can be arcuate such that socket 178 is hemi-spherical in shape. In examples, the wall can have a compound shape with two surfaces, flat or curved, angled with respect to each other. Socket 178 provides a frictional engagement with a neck of a femoral component, such as necks 98A and 98B of adapters 28A and 28B, respectively. Socket 142 can be larger than socket 178 so as to form a well within trialing head 134. As such, a neck extending through socket 178 and into socket 142 can be moved around within the area of trialing head 134 as bushing 150 slides against slide plate 148.

In examples, trialing head 134 can be made from a metallic material, slide plate 148 can be made of a metallic material, and bushing 150 can be made of a polymer material. However, other materials and combinations of materials can be used.

With humeral stem 30 (FIG. 4) inserted into a humerus bone, neck 98A or neck 98B from humeral adapter 28A or humeral adapter 28B can be inserted into socket 178 in bushing 150. Access opening 144 can align with fastener hole 164 such that fastener 152 can be inserted through trialing head 134 into bushing 150. Fastener 152 can include head portion 186A and shaft portion 186B. In examples, fastener 152 can be configured to be captive within humeral head trialing device 130 so that fastener 152 cannot be removed. For example, fastener 152 can include a fixed washer attached to fastener 152 after assembly (e.g., via welding) to prevent shaft portion 186B from being fully retracted from fastener hole 164, or access opening 144 can include a flange that permits fastener 152 to be inserted into trialing head 134 but that engage head portion 186A to prevent shaft portion 186B from being fully retracted from fastener hole 164. Fastener 152 can remain in a loosened position with head portion 186A resting on or near ledge 177 such that slide plate 148 is not pulled into engagement with surface 182 via engagement between threading on fastener 152 and fastener hole 164. With fastener 152 in a loosened position, the position of trialing head 134 relative to the humeral bone can be adjusted. In particular, bushing 150 can slide against slide plate 148 and trialing head 134 can be rotated such that bushing 150 rotates around neck 98A or neck 98B. Trialing head 134 can be translated by translating rails 176A and 176B within slots 166A and 166B of slide plate 148, respectively. Rails 176A and 176B and slots 166A and 166B can be configured so that slide plate 148 and bushing 150 are co-planar, or substantially co-planar, so that bushing 150 is, for example, nested within slide plate 148. Thus, trialing head 134 can be located in any desired positioned relative the humeral bone by the surgeon, thereby changing the offset of humeral head trialing device 130. Once in the desired position, fastener 152 can be changed from the loosened position to a tightened position to lock the configuration of offset slide device 132. In examples, bushing 150 can be crushed or partially crushed between slide plate 148 and trialing head 134.

A driver instrument, e.g., a screw driver or driver instrument 118 of FIG. 8, can engage a drive socket in head portion 186A to rotate shaft portion 186B and to cause slide plate 148 to draw nearer to surface 182 of trialing head 134. Simultaneously, bushing 150 can be sandwiched between portions of slide plate 148 and trialing head 134 to immobilize bushing 150. For example, bushing 150 can be configured to have a surface, edge or ledge that can be pushed into an engaging surface of trialing head 134 as fastener 152 draws slide plate 148 closer to trialing head 134. For example, flanges 174 can be configured to have lengths that allow end surfaces 168 of flanges 174 to be pushed into end wall 143 of socket 142 as fastener 152 is tightened. Engagement between end surfaces 168 and end wall 143 can push flanges 174 toward each other to collapse flanges down around a neck 98A or 98B of an adapter 28A or 28B to tighten the fit. Flanges 174, or similar features, that can collapse around a stem component neck when tightened by a fastener can be incorporated into any of the humeral head trialing devices described herein having a bore that receives the stem component neck. Shaft portion 186B can be advanced into fastener hole 164 to move slide plate 148 toward surface 182 and immobilize bushing 150, or can be retreated from fastener hole 164 to retreat slide plate 148 from surface 182 and free bushing 150 for translation. Thus, frictional engagement between socket 178 and the neck of the humeral stem component can hold the humeral stem component in engagement with offset slide device 132 in an unlocked configuration, and frictional engagement of socket 178 in combination with inward pressure from collapsing of flanges 174 can hold the humeral stem component in engagement with offset slide device 132 in a locked configuration.

Figure 13:
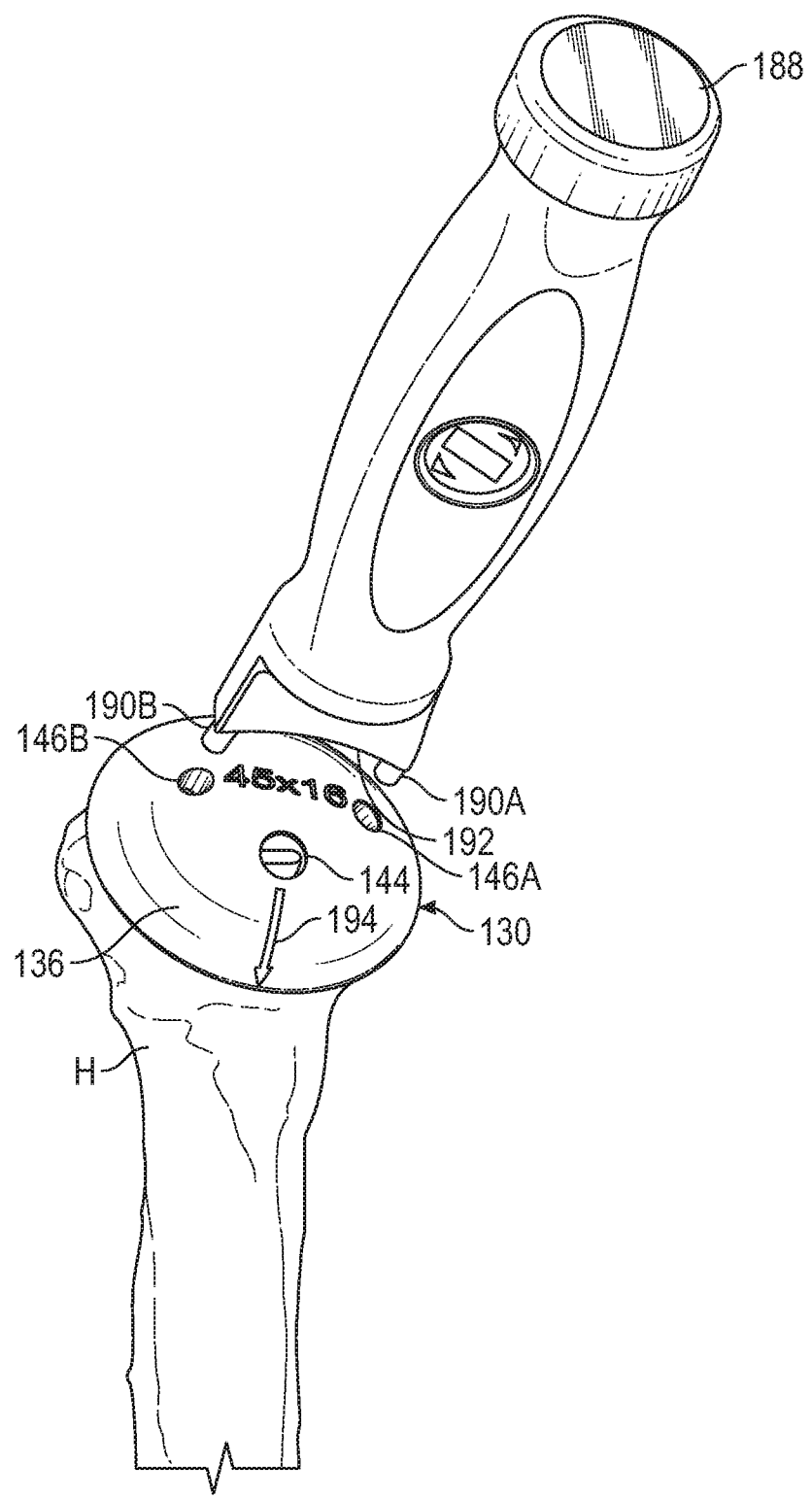
FIG. 13 is a perspective view of the humeral head trialing device of FIGS. 10-12B mounted on a humerus bone and a drive instrument positioned to engage rotational features of the trialing head.

FIG. 13 is a perspective view of humeral head trialing device 130 of FIGS. 10-12B mounted on humerus bone H and drive instrument 188 positioned to engage rotational features 146A and 146B of trialing head 134. Drive instrument 188 can engage trialing head 134 to facilitate rotation and translation of trialing head 134. In particular, drive instrument 188 can include tabs 190A and 190B that are sized and shaped to fit into rotational features 146A and 146B, respectively. In examples, rotational features 146A and 146B can comprise round holes and tabs 190A and 190B can comprise round posts. Drive instrument 188 can also include surface 192 that can be shaped or contoured to engage trialing head 134 and to permit clearance to allow tabs 190A and 190B to enter rotational features 146A and 146B.

When trialing head 134 is first connected to humerus H, trialing head 134 is free to move around. In the orientation shown in FIG. 13, the position of access opening 144 can be changed in the up-and-down direction (relative to the orientation of FIG. 13). Trialing head 134 can be rotated about an axis of the neck inserted into humeral head trialing device 130 to allow the position of access opening 144 to be changed in the side-to-side direction (relative to the orientation of FIG. 13). Once the desired position of trialing head 134 is determined by a surgeon, driver instrument 118 of FIG. 8 can be inserted into access opening 144 to move fastener 152 into a tightened position. The relative position between trialing head 134 and humerus H can be marked, identified or shown using indicator 194. For example, a surgeon can use a tool or marker to indicate on humerus H where indicator 194 should be located in the final position for correlating a position of a humeral head implant.

It is additionally desirable to know where the maximum offset for trialing head 134 is located on humerus H. Indicator 194 can be located on trialing head 134 and can be located in the same place on different trialing heads 134, in the direction where bushing 150 is translated a maximum distance relative to slide plate 148. This allows the surgeon to mark humerus H with a surgical marker or electrocautery (e.g., a Bovie) at the tip of the arrow comprising indicator 194. The mark provided on humerus H at indicator 194 can act as a patient-specific landmark that allows the surgeon to position the final prosthetic implant so that the maximum offset of the final prosthetic implant is aligned with the mark on humerus H. This facilitates the surgeon aligning the final prosthetic implant in the same orientation as trialing head 134. Without a landmark provided on humerus H at indicator 194 a surgeon would have to estimate from memory or anatomic indications by spinning the implant until it appears to be in the same orientation as the trial, which can take more time and is not always as accurate. Furthermore, the final prosthetic implant could be prematurely locked into place while the surgeon is determining a position for the final prosthetic implant. For example, a Morse taper could prematurely engage.

Humeral head trialing device 130 can be removed from humeral adapter 28 and the relative position between bushing 150 and slide plate 148 can be shown, identified, marked, and/or recorded. In particular, with reference to FIG. 11, indicators 156A and 156B can align with size indicia 158A and 158B to indicate a size of a humeral head to implant in the specific patient. Indicators 156A and 156B can be any feature or marking that provides a constant frame of reference on slide plate 148 and that overlaps or otherwise interacts with indicia 158A and 158B.

Each of the hash marks provided by indicia 158A and 158B can correspond to an offset size of a prosthetic humeral head. For example, as can be seen in FIG. 11, size A can correspond to a zero offset where the center of socket 178 aligns with the center of curved articulating surface 136, with sizes B-F indicating progressively larger offsets. Indicators 156A and 156B can include markers that indicate to a user where to look to take the size reading. In the example shown, indicators 156A and 156B comprise arrows pointing to indicia 158A or 158B.

Figure 14A:
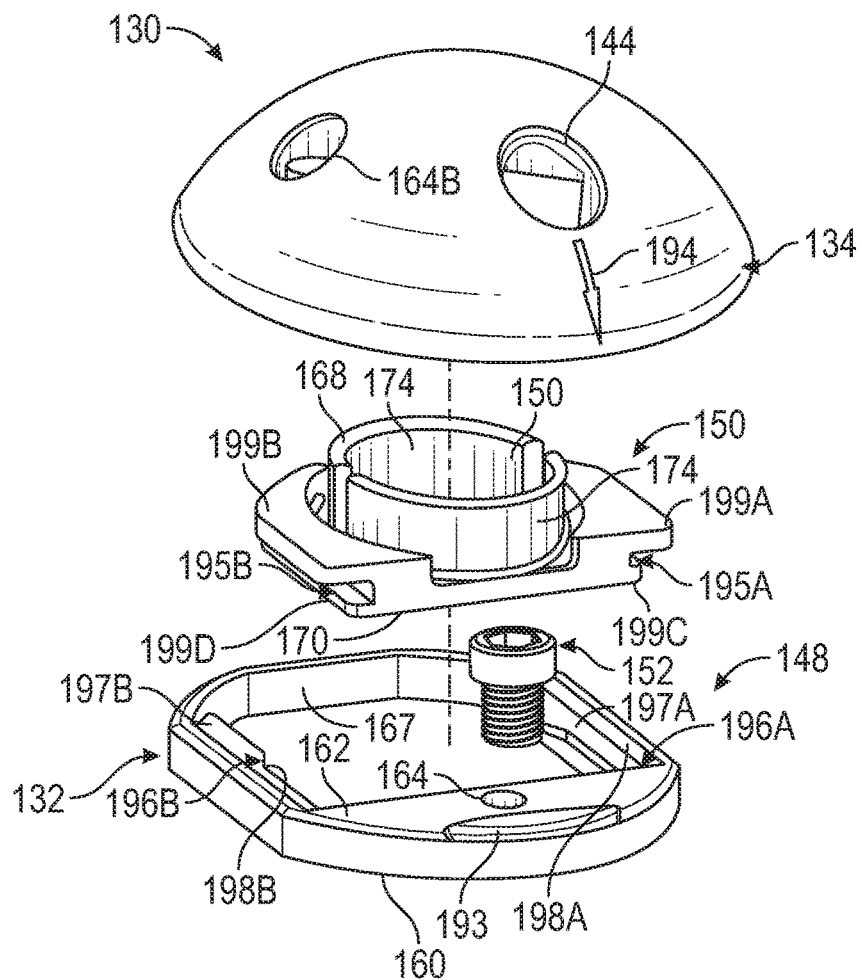
FIG. 14A is an exploded view of an alternative embodiment of the humeral head trialing device of FIGS. 10-12B wherein the bushing includes slots for receiving rails of the slide plate.

FIG. 14A is an exploded view of an alternative embodiment of the humeral head trialing device 130 of FIGS. 10-12B where bushing 150 includes slots 195A and 195B for receiving rails 196A and 196B of slide plate 148. Humeral head trialing device 130 of FIG. 14A is substantially the same as that of FIGS. 12A and 12B except that bushing 150 includes slots 195A and 195B instead of rails 176A and 176B, and slide plate 148 includes rails 196A and 196B instead of slots 166A and 166B.

As can be seen in FIG. 14A, fastener 152 can be configured to not pass through bushing 150. As will be discussed with reference to FIG. 14C, fastener 152 can be tightened to draw slide plate 148 toward trialing head 134 to sandwich bushing 150 between surfaces of trialing head 134 and slide plate 148 to lock the relative positions of bushing 150 and slide plate 148.

Rails 196A and 196B can have wider portions 197A and 197B and narrower portions 198A and 198B, respectively, which can facilitate coupling of bushing 150 to rails 196A and 196B. Slots 195A and 195B can include wider portions 199A and 199B and narrower portions 199C and 199D, respectively, which can facilitate coupling to bushing 150. For example, bushing 150 can be angled with respect to slide plate 148 to allow wider portions 197A and 197B to be inserted into slots 195A and 195B, respectively. Narrower portions 199C and 199D can then be slid underneath rails 196A and 196B to position bushing 150 against slide plate 148. Wider portions 199A and 199B can then rest on wider portions 197A and 197B and narrower portions 198A and 198B of rails 196A and 196B, while narrower portions 199C and 199D are disposed underneath wider portions 197A and 197B. Rails 196A and 196B are, however, longer than slots 195A and 195B so that bushing 150 can translate within aperture 167. Rails 196A and 196B and slots 195A and 195B can be configured so that slide plate 148 and bushing 150 are co-planar, or substantially co-planar, so that bushing 150 is, for example, nested within slide plate 148.

Figure 14B:
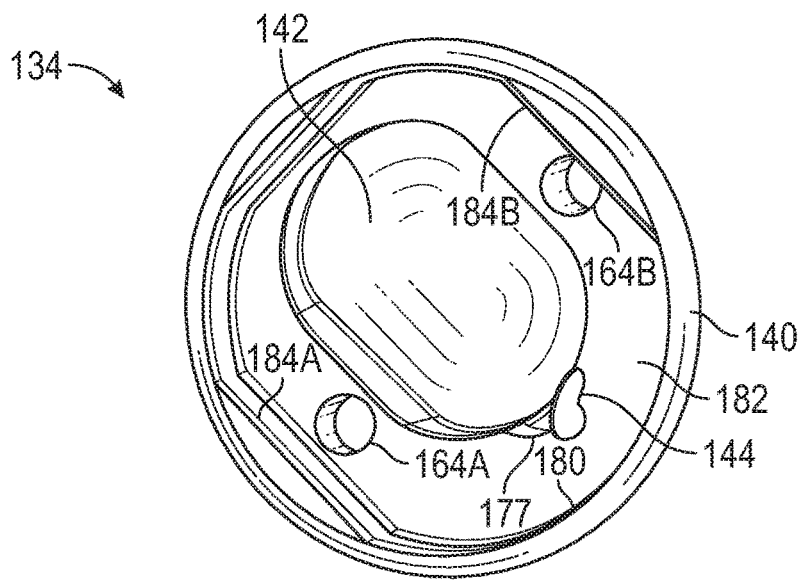
FIG. 14B is a perspective view of a trialing head used in the humeral head trialing device of FIG. 14A showing a well and a socket for receiving the bushing and slide plate.

FIG. 14B is a perspective view of trialing head 134 used in humeral head trialing device 130 of FIG. 14A showing socket 142 and recess 180 for receiving bushing 150 and slide plate 148. Recess 180 is configured to mate with the edge of slide plate 148 so that offset slide device 132 can be tightly fit into recess 180. Flats 184A and 184B of recess 180 along with corresponding flats on slide plate 148 prevent offset slide device 132 from rotating within recess 180. When slide plate 148 is seated in recess 180, sixth major surface 162 can abut surface 182 of trialing head 134. Additionally, access opening 144 can align with fastener hole 164. Fastener 152 can be inserted into access opening 144, passed through ledge 177 in trialing head 134 and threaded into fastener hole 164.

Figure 14C:
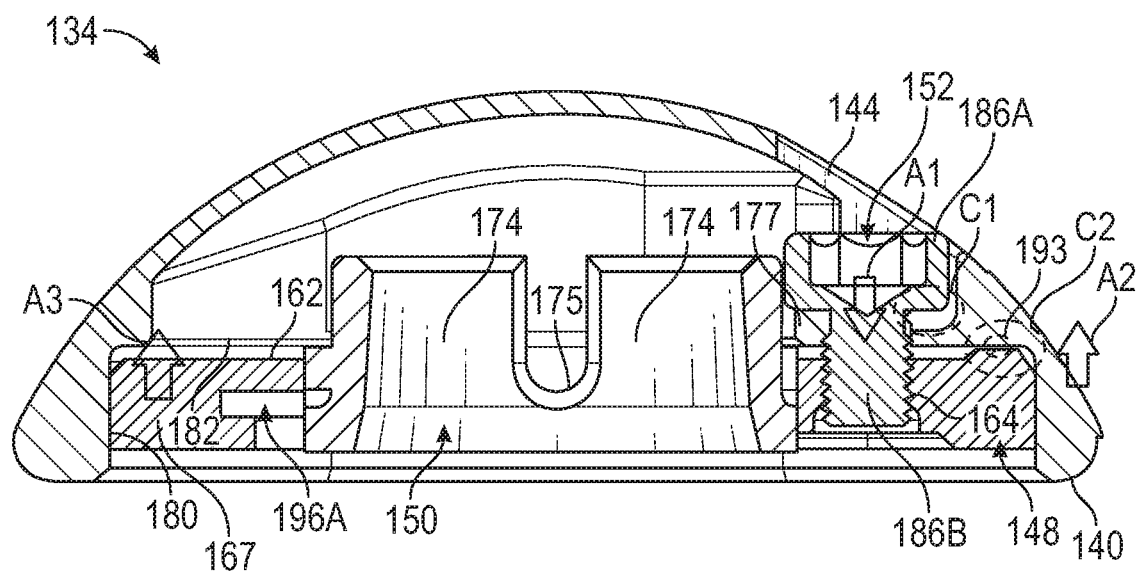
FIG. 14C is a cross-sectional view of the humeral head trialing device of FIG. 14A showing interacting forces generated by a fastener.

FIG. 14C is a cross-sectional view of humeral head trialing device 130 of FIG. 14A showing interacting forces generated by fastener 152. Fastener 152 is threaded down into fastener hole 164 as shown by arrow A1 to bring head portion 186A into contact with ledge 177 at callout C1. Additional threading or tightening of shaft portion 186B causes slide plate 148 to move upward, as shown by arrow A2. Slide plate 148 is then pushed upward against surface 182 as shown in callout C2. Sixth major surface 162 can include platform 193 that is elevated from a remaining portion of sixth major surface 162. Platform 193 can act as a lever mechanism when fastener 152 draws slide plate 148 toward surface 182. For example, slide plate 148 will rotate at platform 193 as fastener hole 164 is drawn closer to surface 182, which can cause the end of slide plate 148 opposite of platform 193 to rotate toward surface 182, as shown by arrow A3. The lever action provided by platform 193 can improve the friction force that clamps down against bushing 150 by causing both ends of slide plate 148 to be drawn in tight to surface 182. The lever action additionally can prevent slide plate 148 from rocking or rotating about bushing 150, which can interfere with alignment between humeral head trialing device 130 and a humeral stem component. As mentioned, bushing 150 can include cut-outs 175 to form flanges 174 that permit bushing 150 to flex and receive neck 98A or 98B.

Figure 15A:
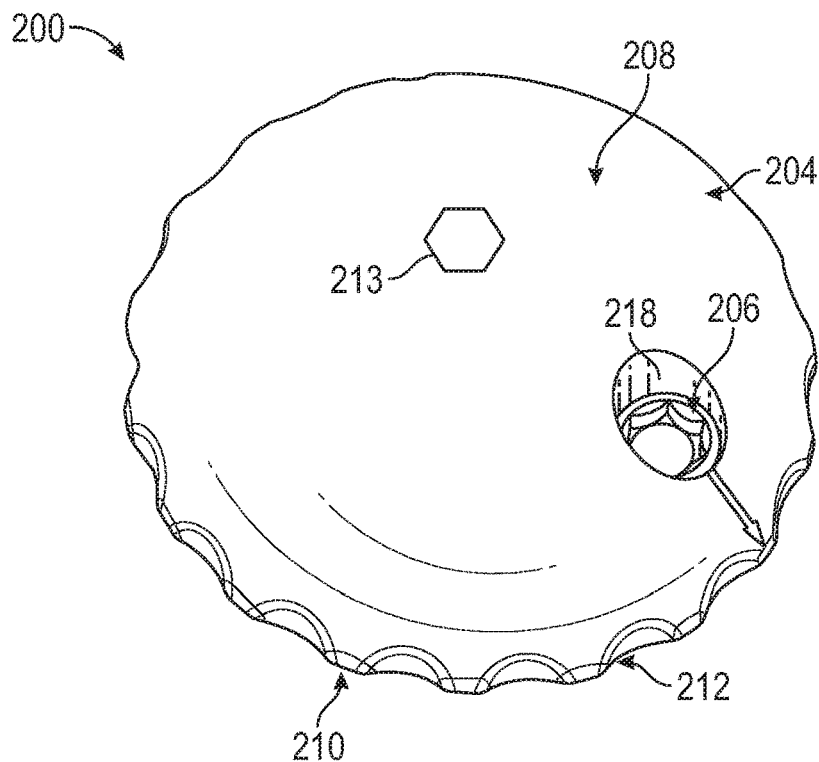
FIG. 15A is a top perspective view of another embodiment of a humeral head trialing device for use with the humeral head prosthetic device system of FIG. 4.
Figure 15B:
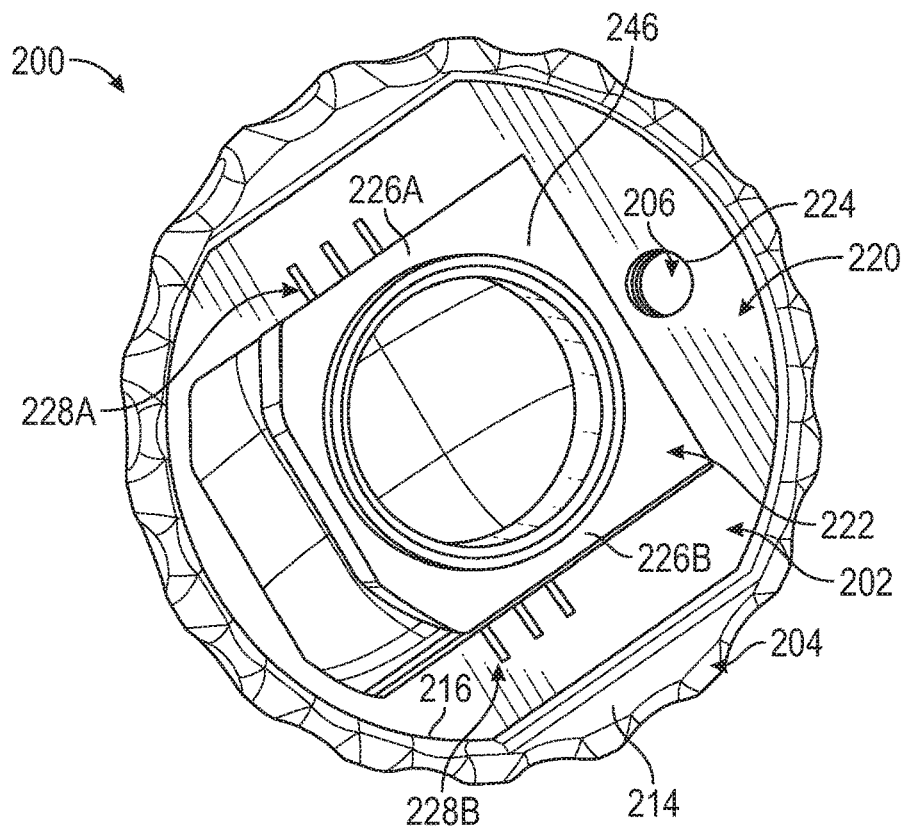
FIG. 15B is a bottom perspective view of the humeral head trialing device of FIG. 15A showing another embodiment of an offset slide device within a trialing head.

FIG. 15A is a top perspective view of humeral head trialing device 200 for use with humeral head prosthetic device system 10 of FIG. 4. FIG. 15B is a bottom perspective view of humeral head trialing device 200 of FIG. 15A showing offset slide device 202 within trialing head 204.

Humeral head trialing device 200 is similar to other humeral head trialing device described herein and can be used with features described with reference to the other embodiments. Humeral head trialing device 200 can include fastener 206 for locking offset slide device 202.

Trialing head 204 can comprise curved articulating surface 208, edge perimeter 210 having scallops 212, interior surface 214, socket 216 and access opening 218. Offset slide device 202 can include trial offset plate 220 and trial offset slide 222. Trial offset plate 220 and trial offset slide 222 can be coupled together using fastener 206. Trial offset plate 220 and trial offset slide 222 can operate in a similar fashion as mounting plate 40 and adapter coupling plate 42 of humeral head trialing device 36, respectively. However, rather than adapter coupling plate 42 sliding against mounting plate 40 in an abutting relationship, trial offset slide 222 can include rails that are captured within channels of trial offset plate 220.

Trial offset plate 220 is inserted into socket 216 of trialing head 204 and can be held in place by frictional interaction between trial offset plate 220 and trialing head 204 at socket 216. Fastener 206 can be extended into access opening 218 to engage fastener bore 224 in trial offset plate 220 to prevent trial offset plate 220 from separating from trialing head 204. Trial offset slide 222 can slide between trialing head 204 and trial offset plate 220 such that indicators 226A and 226B can align with size indicia 228A and 228B on trial offset plate 220. Fastener 206 can be adjusted to immobilize trial offset slide 222 relative to trial offset plate 222.

Figure 16:
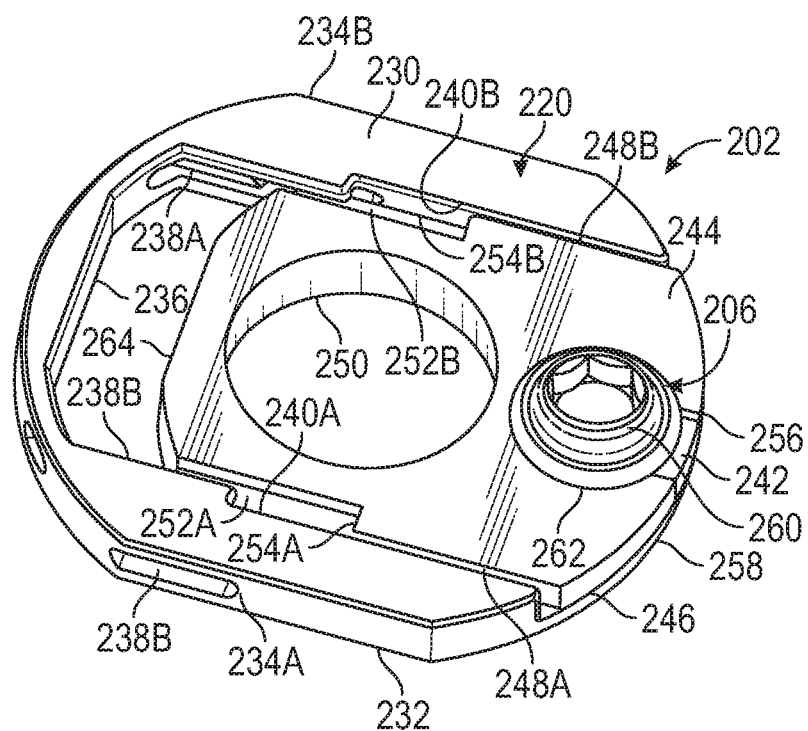
FIG. 16 is a top perspective view of a first embodiment of the offset slide device including a trial offset plate, trial offset slide and a locking screw.

FIG. 16 is a top perspective view of a first embodiment of offset slide device 220 including a trial offset plate 220, trial offset slide 222 and fastener 206.

Trial offset plate 220 can include seventh major surface 230, eighth major surface 232, flats 234A and 234B, aperture 236, slots 238A and 238B (FIG. 20A), cutouts 240A and 240B, post 242 and fastener bore 224 (FIG. 15). Trial offset slide 222 can include ninth major surface 244, tenth major surface 246, flats 248A and 248B, coupling bore 250, rails 252A and 252B, cutouts 254A and 254B and notch 256.

Trial offset plate 220 can be configured to be positioned within socket 216 of trialing head 204 (FIG. 15). Flats 234A and 234B can prevent trial offset plate 220 from rotating within socket 216. Aperture 236 can be configured to receive trial offset slide 222 and can comprise a U-shaped cut-out in trial offset plate 220. Aperture 236 can be partially bounded by crosspiece 258 on which post 242 can be disposed. Aperture 236 can include slots 238A and 238B and cutouts 240A and 240B that can mate with trial offset slide 222.

Rails 252A and 252B of trial offset slide 222 can be inserted into slots 238A and 238B, respectively. Rails 252A and 252B and slots 238A and 238B can be configured to hold trial offset slide 222 co-planar, or substantially co-planar, with trial offset plate 220 such that trial offset slide 222 can be nested within trial offset plate 220. Rails 252A and 252B and slots 238A and 238B can be shaped and configured to allow cutouts 240A and 240B to mate with cutouts 254A and 254B, respectively, to, for example, limit movement of trial offset slide 222.

Figure 20A:
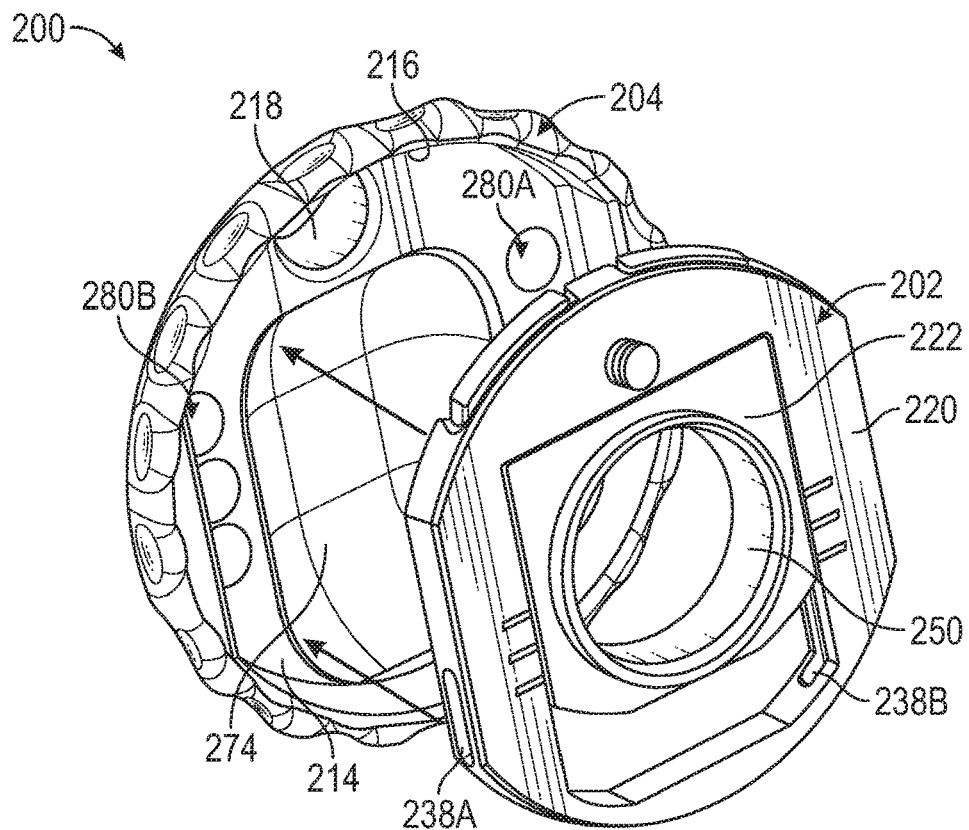
FIG. 20A is a partially exploded view of the humeral head trialing device of FIGS. 15A and 15B showing the offset slide device of FIGS. 15 and 16 positioned relative to the trial mechanism well of the trialing head of FIGS. 15 and 19.
Figure 20B:
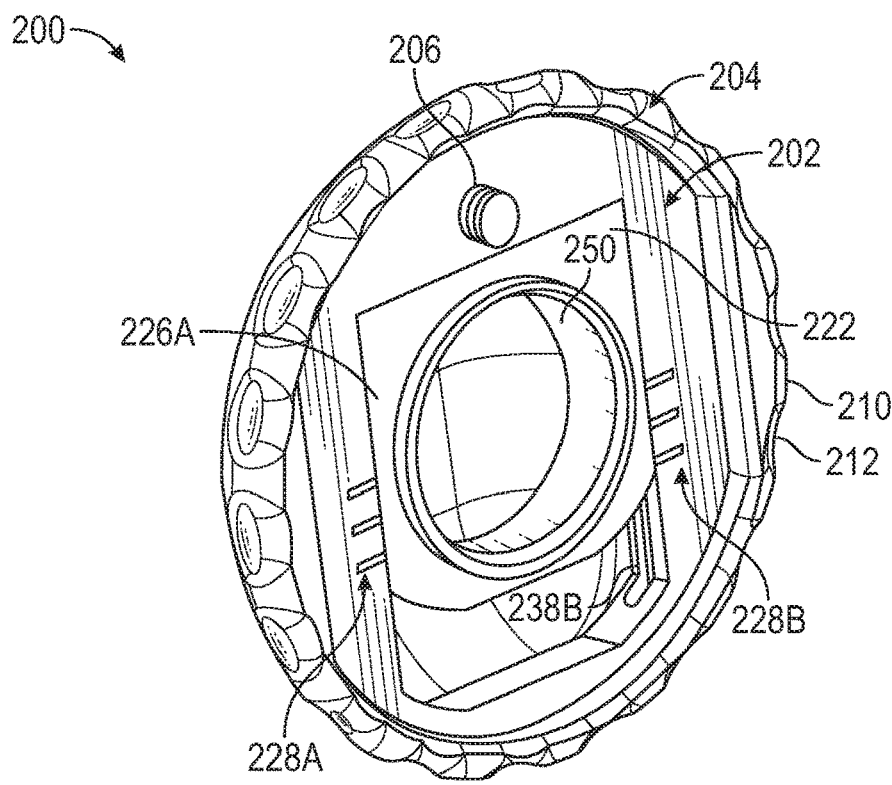
FIG. 20B is a perspective view of the humeral head trialing device of FIGS. 15A and 15B showing the offset slide device of FIG. 20A inserted into the trial mechanism well.

In the centered position, as shown in FIG. 16, trial offset slide 222 is positioned all the way to the right (with respect to the orientation of FIG. 16) such that notch 256 engages post 242. The centered position is also shown in FIGS. 20A and 20B. With notch 256 and post 242 engaged, a portion of rails 252A and 252B remain engaged with slots 238A and 238B, respectively. As such, trial offset slide 220 is supported within trial offset plate 220. Fastener 206 can be threaded into post 242 at fastener bore 224. Fastener 206 can include head 260 that can include flange 262 that can press down on trial offset slide 222 to press trial offset slide 222 against crosspiece 258, thereby immobilizing trial offset slide 222.

Figure 20C:
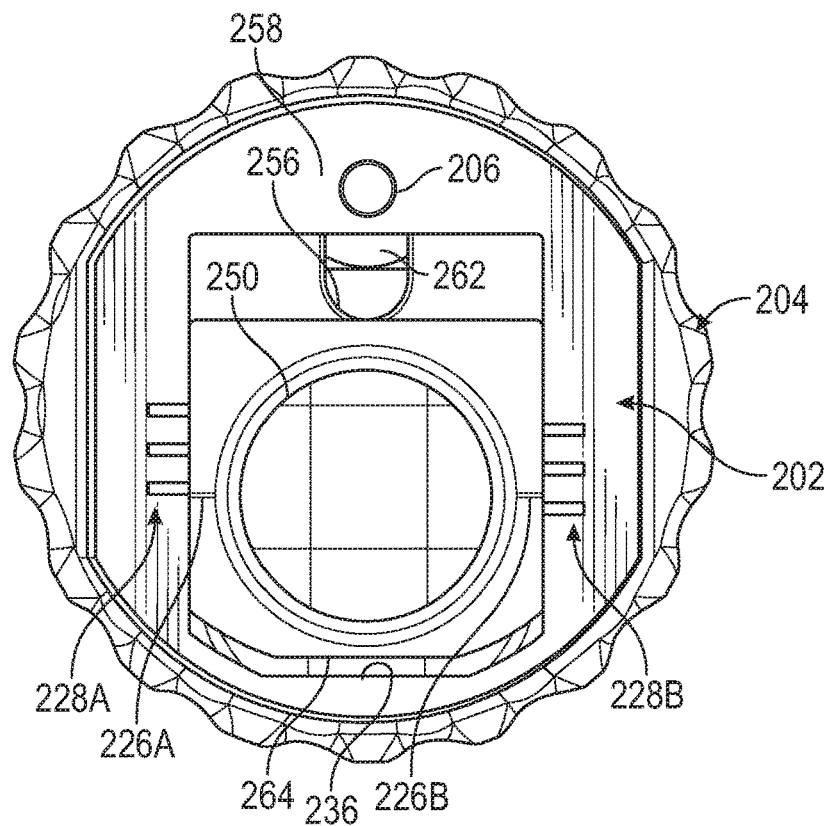
FIG. 20C is a bottom plan view of the humeral head trialing device of FIGS. 15A and 15B showing the trial offset slide translated within a groove of the trial offset plate to expose a fastener channel.

Trial offset slide 222 can be moved away from the centered position of FIG. 16 to a plurality of offset positions by moving trial offset slide 222 to the left (with respect to the orientation of FIG. 16). A partially offset position is shown in FIG. 20C. In a fully offset position, aperture 236 and cutouts 240A and 240B are shaped to engage with end 264 and cutouts 254A and 254B, respectively, while rails 252A and 252B slide in slots 238A and 238B, respectively. With end 264 directly engaging aperture 236, trial offset slide 222 can be positioned away from post 242. However trial offset slide 222 can remain supported by crosspiece 258 such that head 260 and flange 262 of fastener 206 can push trial offset slide 222 against crosspiece 258 to immobilize trial offset slide 222 (See FIG. 20C). As shown in FIG. 15, trial offset slide 222 can be positioned to align one of indicators 226A and 226B with one of size indicia 228A and 228B. Indicators 226A and 226B are positioned so that only one size indicia will be indicated for the offset of trial offset slide 222. As discussed above, one of sizes A-F can be selected by indicators 226A and 226B by pointing to size indicia 228A and 228B, for example.

Figure 17:
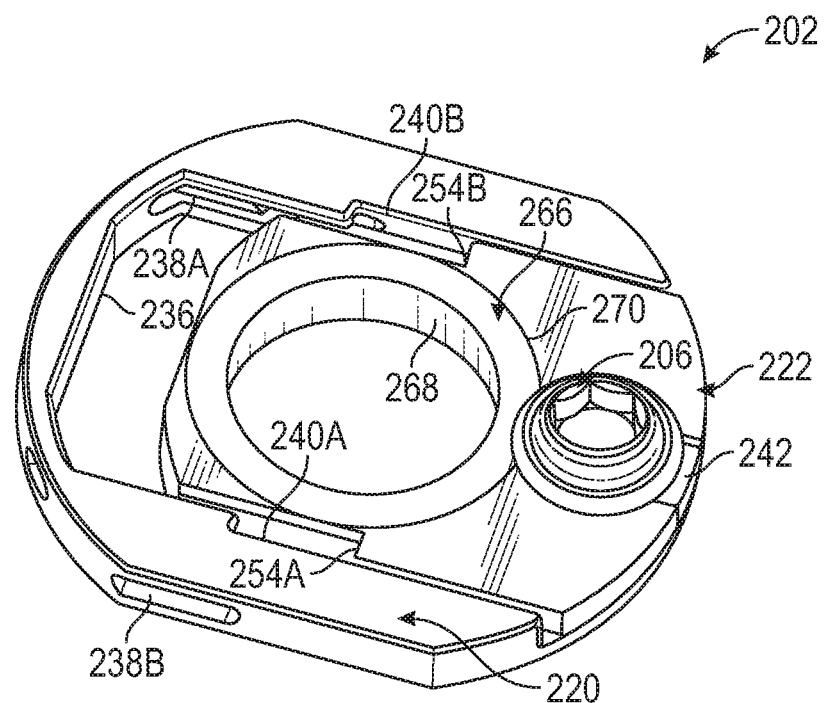
FIG. 17 is a top perspective view of a second embodiment of the offset slide device including a trial offset plate and a trial offset slide with a bushing.

FIG. 17 is a top perspective view of a second embodiment of offset slide device 202 including trial offset plate 220 and trial offset slide 222 with bushing 266. Trial offset plate 220 of FIG. 17 can function in the same manner as that of FIG. 16 except that coupling bore 250 is provided with bushing 266. Bushing 266 can function as a liner to coupling bore 250 that facilitates engagement with an adapter neck, such as neck 98A or neck 98B of humeral adapter 28A and humeral adapter 28B, respectively. Trial offset slide 222 can be made of a rigid metallic material and bushing 266 can be comprised of a resilient material, such as a plastic or polymer. Bushing 266 can soften the engagement with the humeral adapter, prevent damage to the humeral adapter and facilitate affixation to the humeral adapter. Bushing 266 can include axial portion 268 that extends across coupling bore 250 and one or more flange portions 270 that can extend radially across ninth and tenth major surfaces 244 and 246, respectively, to inhibit bushing 266 from separating from coupling bore 250.

Bushing 266 can be configured as a separate piece that can be installed into and removed from trial offset slide 222. Thus, a bushing 266 having a different sized axial portion 268 (e.g., a different diameter socket) can be swapped into and out of trial offset slide 222. Additionally, other bushing components can be attached to trial offset slide 222, such as those including a projection feature (e.g., a projection feature similar to projection feature 272 of FIG. 18) instead of a socket can be attached to trial offset slide 222.

Figure 18:
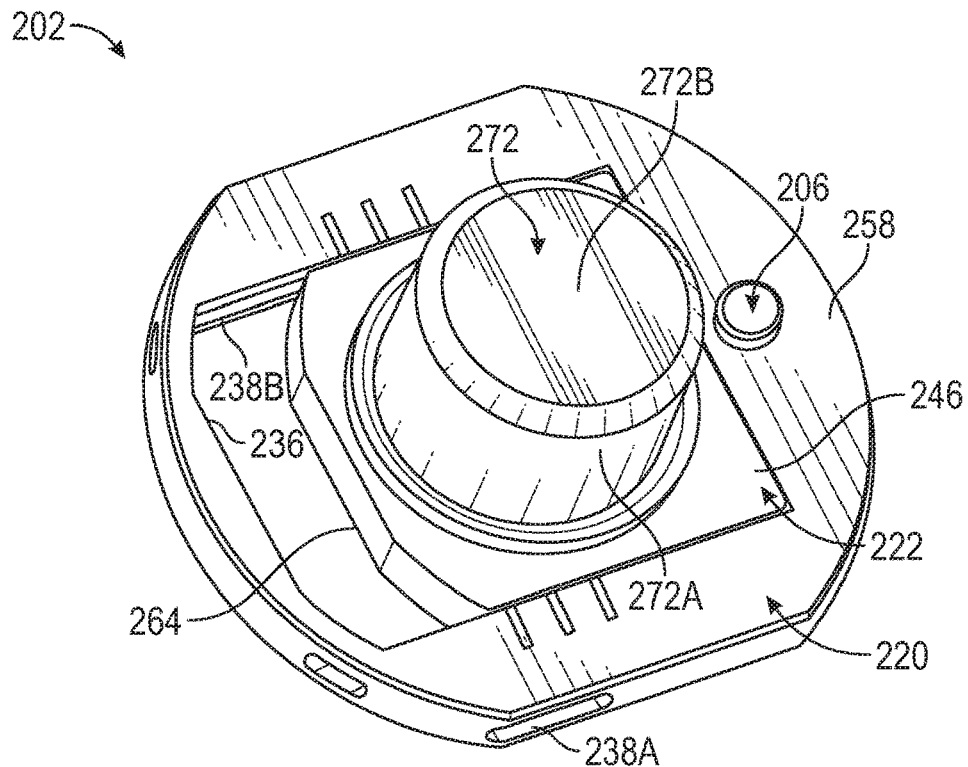
FIG. 18 is a bottom perspective view of a third embodiment of the offset slide device including a trial offset plate and a trial offset slide with a projection feature.

FIG. 18 is a bottom perspective view of a third embodiment of offset slide device 202 including trial offset plate 220 and trial offset slide 222 with projection feature 272. Trial offset plate 220 of FIG. 18 can function in the same manner as that of FIG. 16 except that coupling bore 250 is provided with projection feature 272. Projection feature 272 can include cylindrical portion 272A and end wall 272B. Projection feature 272 can be solid or hollow. Projection feature 272 can function to interact with a female socket on a humeral adapter or humeral stem, such as humeral adapter 28A, humeral adapter 28B, or humeral stem 30. In various examples, projection feature 272 can be integral with trial offset slide 222 and coupling bore 250 such that cylindrical portion 272A extends from tenth major surface 246. In additional examples, projection feature 272 can be a separate component from trial offset slide 222 that can be mated with coupling bore 250. As examples, projection feature 272 can be inserted into coupling bore 250 from ninth major surface 244 so that cylindrical portion 272A can extend through trial offset slide 222 and beyond tenth major surface 246. Additionally, projection feature 272 can be threaded into ninth major surface 244 at or adjacent coupling bore 250.

Projection feature 272, or a similar feature, can be included in any of the humeral head trialing devices described herein. For example, adapter coupling hole 68 of FIGS. 3A and 3B can include a cylindrical portion projecting from adapter coupling plate 42 and an end wall closing off the cylindrical portion. Likewise, socket 178 of FIG. 11, coupling bore 250 of FIG. 16 and bushing 266 of FIG. 17 can include a projection feature similar to projection feature 272.

Figure 19:
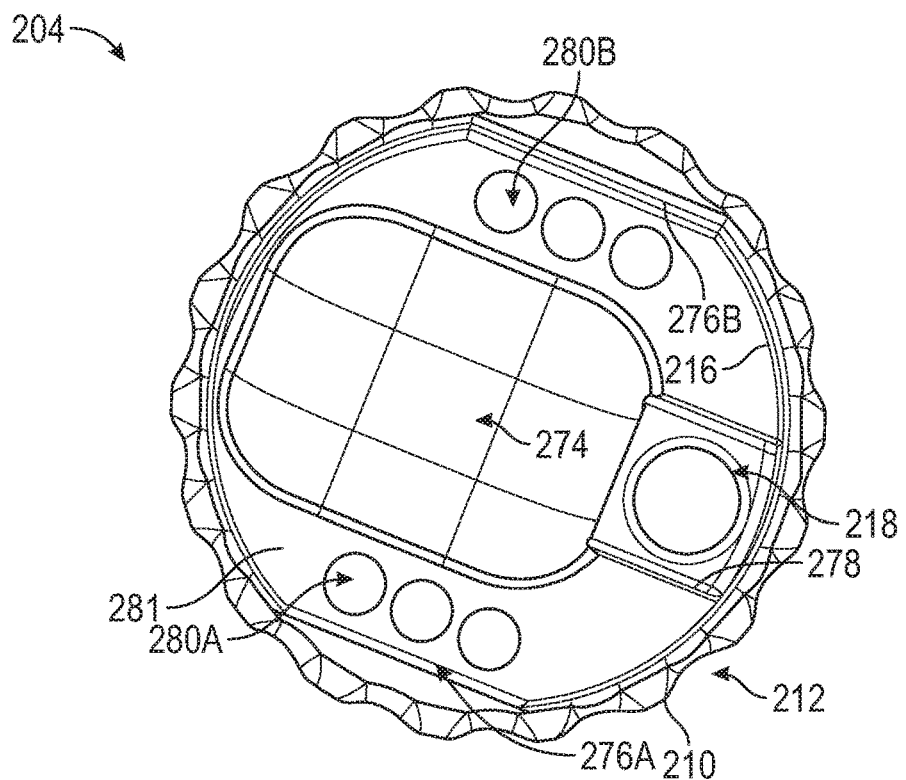
FIG. 19 is a bottom view of the trialing head of FIGS. 15A and 15B showing a trial mechanism well, gripping features, anti-rotation features and retention features.

FIG. 19 is a bottom view of trialing head 204 of FIGS. 15A and 15B showing trial mechanism well 274, scallops 212, anti-rotation features 276A and 276B, and retention features 280A and 280B.

Edge perimeter region 210 can include scallops 212 that can act as gripping features to facilitate rotation of trialing head 204 by a surgeon. For example, scallops 212 can increase friction between trialing head 204 and a hand of the surgeon to allow trialing head 204 to be rotated on the neck of the adapter to which it is mounted (see FIG. 20D).

Although depicted as semi-circular scallops, edge perimeter region 210 and trialing head 204 can include other gripping features with different shapes. For example, edge perimeter 210 can be provided with scoring, crenellations, knurling and the like. Additionally, trialing head 204 can be provided with other rotational features that facilitate gripping and rotating of trialing head 204 by a surgeon. For example, trialing head 204 can include various sockets (e.g., sockets 146A and 146B of FIG. 10) to facilitate coupling with a tool (e.g., instrument 188 of FIG. 13). Furthermore, trialing head 204 could include a hex socket 213 at its center to mate with a driver instrument, such as a hex key, an Allen wrench or the like.

Trial mechanism well 274 can comprise a thinned portion of trialing head 204, e.g., a portion of trial mechanism well 274 that has a thickness that is smaller than other portions of trial mechanism well 274, to provides space within trialing head 204 to accommodate offset slide device 202. Trial mechanism well 274 can be smaller than socket 216 to allow trial offset plate 220 to be tightly fit with trialing head 204. Trial mechanism well 274 can be located opposite coupling bore 250 when assembled with offset slide device 202 and can be wide enough to allow coupling bore 250 to move from the centered position of FIG. 20B to various offset positions, such as shown in FIG. 20C, with a humeral adapter neck inserted therein. Trial mechanism well 274 can be deep enough to accommodate the neck of the adapter inserted into coupling bore 250, as well as any projection feature 272 that can be extended from coupling bore 250. Trial mechanism well 274 can include pocket 278 that can be included to provide space for head 260 and flange 262 of fastener 206. Pocket 278 need not be contiguous with trial mechanism well 274. Pocket 278 can thus be provided at the location of access opening 218, and pocket 278 can surround access opening 218.

Inner surface 281 of trialing head 204 can include retention features 280A and 280B. Retention features 280A and 280B can be configured to assist with holding trial offset plate 220 within socket 216 in addition to or alternatively to any frictional fit or press fit forces provided by the interaction of trial offset plate 220 and pocket 216. For example, pocket 216 can be shaped to have approximately the same outer perimeter shape as trial offset plate 220 to hold trial offset plate 220 snuggly in place. However, in order to facilitate insertion of trial offset plate 220 so that, for example, a surgeon does not have to force trial offset plate 220 into pocket 216, trialing head 204 can be provided with other features to hold trial offset plate 220 in place. Retention features 280A and 280B can comprise magnets that are embedded into inner surface 281 of trialing head 204. In examples where trial offset plate 220 is fabricated from metal materials, the magnets of retention features 280A and 280B can hold onto trial offset plate 220. Retention features 280A and 280B can be press fit into sockets within inner surface 281 and can be additionally or alternatively held in place with adhesive. In other examples, retention features 280A and 280B can comprise adhesive pads deposited onto inner surface 281 to hold onto trial offset plate 220 by adhesive forces.

FIG. 20A is a partially exploded view of humeral head trialing device 200 of FIGS. 15A and 15B showing offset slide device 202 of FIGS. 15 and 16 positioned relative to trial mechanism well 274 of trialing head 204 of FIGS. 15 and 19. In order to assemble offset slide device 202 with trialing head 204, trial offset plate 220 can be aligned to be generally parallel to interior surface 214 of trialing head 204. Trial offset plate 220 can also be aligned with socket 216 such that the shape of trial offset plate 220 aligns with the shape of socket 216. Trial offset plate 220 can then be inserted into socket 216 with trial offset slide 222 already coupled to trial offset plate 220. With trial offset plate 220 inserted into socket 216, retention features 280A and 280B can couple to trial offset plate 220 to prevent trial offset plate 220 from dislodging from socket 216.

FIG. 20B is a perspective view of humeral head trialing device 200 of FIGS. 15A and 15B showing offset slide device 202 of FIG. 20A inserted into trial mechanism well 274. As shown, trial offset slide 222 can be positioned partially behind trial offset plate 220 so that trial offset slide 222 cannot be separated from humeral head trialing device 200 when assembled. In particular, rails 252A and 252B can be retained within slots 238A and 238B (FIG. 16), respectively, to contain trial offset slide 222. Trial offset slide 222 is shown in the centered position where indicator 226A aligns with one of size indicia 228A that corresponds to a centered position of trialing head 204, which can comprise "size A" as discussed above. Fastener 206 can be set to a loosened position to permit trial offset slide 222 to slide within trial offset plate 220.

FIG. 20C is a bottom plan view of humeral head trialing device 200 of FIGS. 15A and 15B showing trial offset slide 222 translated within slots 238A and 238B of trial offset plate 220 to expose notch 256. Trial offset slide 222 is translated away from the centered position of FIG. 20B to an offset position where indicator 226A aligns with one of size indicia 228A, which can comprise "size E" as discussed above. Flange 262 of fastener 206 can extend beyond crosspiece 258 to overlap with portions of trial offset slide 222 at notch 256. Thus, trial offset slide 222 can be locked into position relative to trial offset plate 220 by tightening of fastener 206. Fastener 206 can be positioned on post 242 and flange 262 can be sized to engage trial offset slide 222 even when end 264 is positioned to abut aperture 236. Fastener 206 can remain in a loosened position to permit trial offset slide 222 to slide within trial offset plate 220 so that trialing head 204 can be adjusted relative to a humeral stem implant.

Figure 20D:
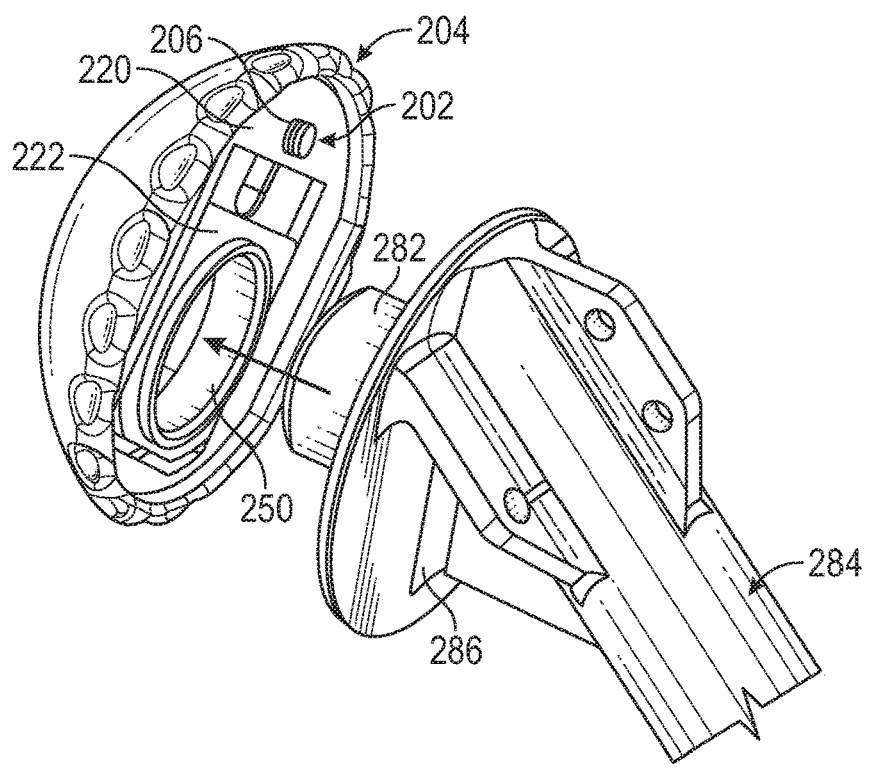
FIG. 20D is a perspective view of the humeral head trialing device of FIGS. 15A and 15B showing the offset slide device aligned with a neck of a humeral stem.

FIG. 20D is a perspective view of humeral head trialing device 200 of FIGS. 15A and 15B showing offset slide device 202 aligned with neck 282 of humeral stem 284. Neck 282 can be inserted into coupling bore 250 in order to seat humeral head trialing device 200 onto humeral stem 284. Humeral stem 284 can include flange 286 that can be configured to be positioned proximate a resected humeral bone surface. Trialing head 204 can be positioned relative to flange 286 by rotating coupling bore 250 about neck 282 and translating trial offset slide 222 relative to trial offset plate 220.

Figure 20E:
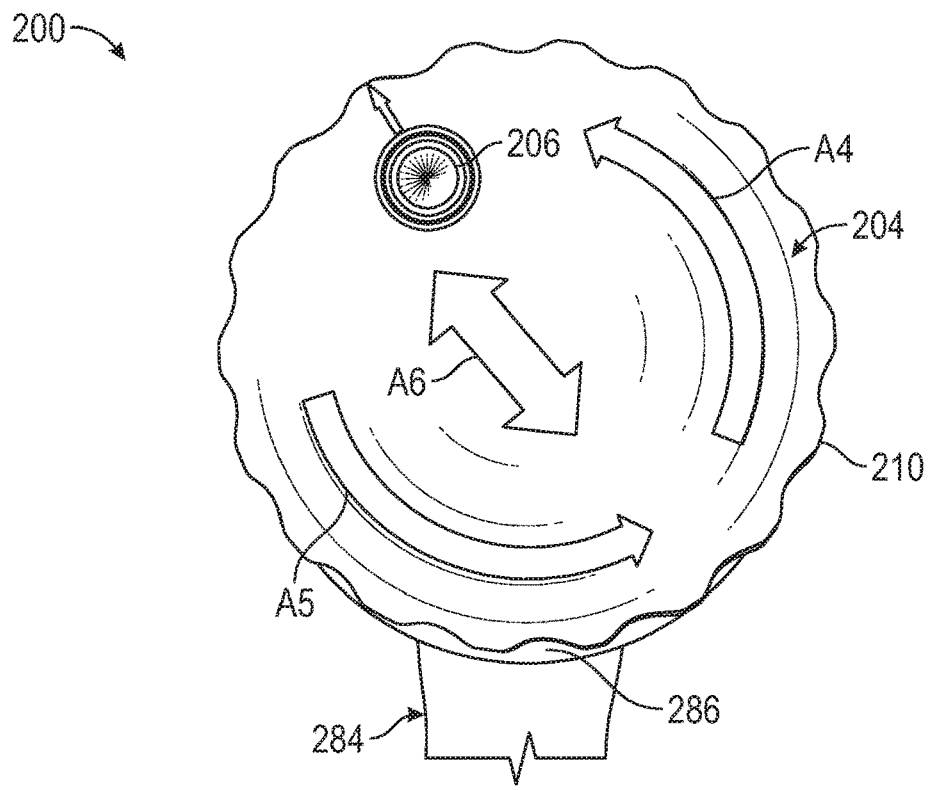
FIG. 20E is a front plan view of the humeral head trialing device of FIGS. 15A and 15B attached to the humeral stem to illustrate rotational and translational movement capabilities of the trialing head.

FIG. 20E is a front plan view of humeral head trialing device 200 of FIGS. 15A and 15B attached to humeral stem 284 to illustrate rotational and translational movement capabilities of trialing head 204. Edge perimeter 210 can approximately match the circumference of flange 286. Thus, when coupling bore 250 of trial offset slide 222 is centered relative to trialing head 204, edge perimeter 210 can approximately overlap with the edge of flange 286. In other words, the centers of trialing head 204, coupling bore 250 and flange 286 can all be aligned so that trialing head 204 can completely cover flange 286. However, using offset slide device 202, trialing head 204 can be rotated in clockwise and counterclockwise directions, as shown by arrows A4 and A5, and can be translated in two directions along a midline of trialing head 204 through which fastener 206 passes, as shown by arrow A6, to reposition the center of trialing head 204 relative to flange 286, which can partially uncover portions of flange 286.

Figure 20F:
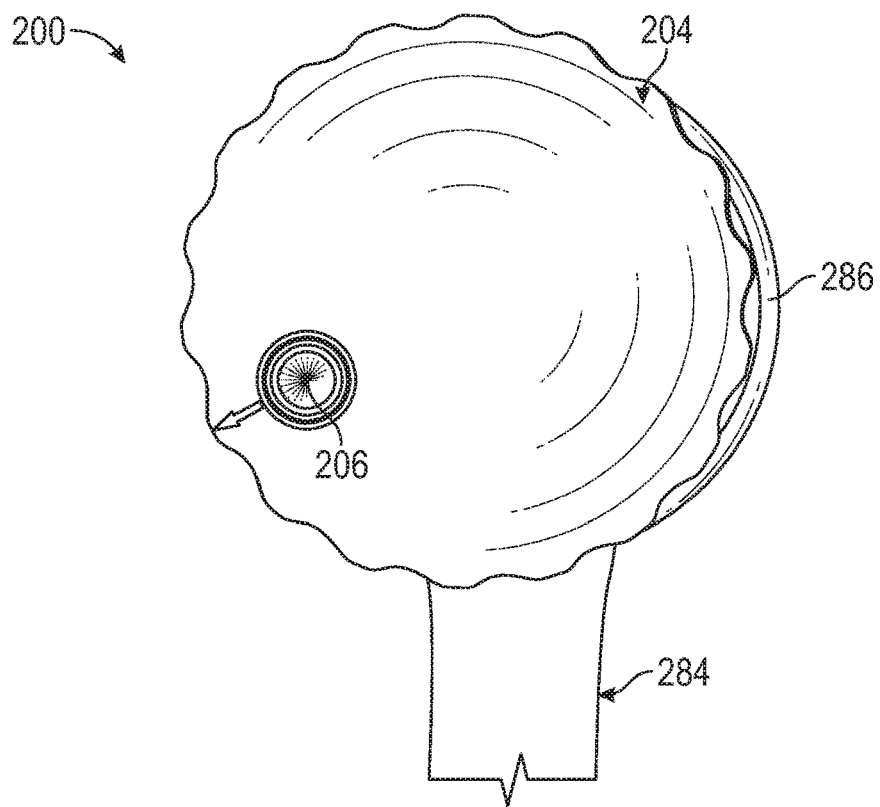
FIG. 20F is a front plan view of the humeral head trialing device of FIGS. 15A and 15B showing the trialing head rotated and translated from the position of FIG. 20E.

FIG. 20F is a front plan view of humeral head trialing device 200 of FIGS. 15A and 15B showing trialing head 204 rotated and translated from the position of FIG. 20E. Trialing head 204 is shown rotated approximately ninety degrees from the position of FIG. 20E and then translated down and to the left (relative to the orientation of FIGS. 20E and 20F) to expose a right-hand portion of flange 286. The combination of rotation provided by coupling bore 250 and the translation provided by trial offset slide 222 can allow the center of trialing head 204 to be positioned anywhere within an offset radius of the center of flange 286. The offset radius can be determined by the stroke length of trial offset slide 222 from the centered position (i.e., the position of FIG. 20B) to the maximum offset position where end 264 abuts aperture 236 (See FIG. 20C).

Various Notes & Examples

Example 1 can include or use subject matter such as a system for aligning a prosthetic head component with a prosthetic stem, the system can comprise: a mounting plate that can comprise: a first major surface; a second major surface opposing the first major surface; an adapter accommodation hole extending through from the first major surface to the second major surface; and sizing indicia located on the second major surface; a first fastener extending from the mounting plate; and an adapter coupling plate slidably engaged with the mounting plate, the adapter coupling plate can comprise: a third major surface facing in a direction of the first major surface; a fourth major surface opposing the third major surface; an adapter coupling hole extending through from the third major surface to the fourth major surface, the adapter coupling hole surrounded by the adapter accommodation hole; and an indicator located on the fourth major surface to point to various portions of the sizing indicia as the adapter coupling plate slides against the mounting plate at the first slot.

Example 2 can include, or can optionally be combined with the subject matter of Example 1, to optionally include the prosthetic head component, the prosthetic head component can comprise: an outer curved surface for approximating an anatomic articulation surface of an anatomic head; and an inner surface having a cavity that accepts the first major surface of the mounting plate.

Example 3 can include, or can optionally be combined with the subject matter of one or any combination of Examples 1 or 2 to optionally include a fastener that can extend into the prosthetic head component so as to be accessible from the outer curved surface.

Example 4 can include, or can optionally be combined with the subject matter of one or any combination of Examples 1 through 3 to optionally include a prosthetic head component that can include a first access hole in the outer curved surface aligned with the first fastener.

Example 5 can include, or can optionally be combined with the subject matter of one or any combination of Examples 1 through 4 to optionally include a stem adapter that can comprise: a body for engaging a socket of the prosthetic stem; and a neck extending from the body frictionally engaged with the adapter coupling hole and passing freely into the adapter accommodation hole.

Example 6 can include, or can optionally be combined with the subject matter of one or any combination of Examples 1 through 5 to optionally include a prosthetic stem, wherein the prosthetic stem can comprise a humeral stem and the prosthetic head component comprises a humeral head.

Example 7 can include, or can optionally be combined with the subject matter of one or any combination of Examples 1 through 6 to optionally include a magnet located in the cavity to engage the first major surface of the mounting plate.

Example 8 can include, or can optionally be combined with the subject matter of one or any combination of Examples 1 through 7 to optionally include a mounting plate that is friction fit into the cavity of the prosthetic head component.

Example 9 can include, or can optionally be combined with the subject matter of one or any combination of Examples 1 through 8 to optionally include a first deformable sleeve to engage the first fastener.

Example 10 can include, or can optionally be combined with the subject matter of one or any combination of Examples 1 through 9 to optionally include an outer curved surface of the prosthetic head component that includes a rotational feature.

Example 11 can include, or can optionally be combined with the subject matter of one or any combination of Examples 1 through 10 to optionally include a rotational feature that comprises scallops disposed around a periphery of the outer curved surface.

Example 12 can include, or can optionally be combined with the subject matter of one or any combination of Examples 1 through 11 to optionally include a rotational feature that comprises a socket disposed in the outer curved surface.

Example 13 can include, or can optionally be combined with the subject matter of one or any combination of Examples 1 through 12 to optionally include an inner surface of the prosthetic head component that is textured to increase frictional engagement with bone.

Example 14 can include, or can optionally be combined with the subject matter of one or any combination of Examples 1 through 13 to optionally include a first fastener that is threaded into the mounting plate and passes through the adapter coupling plate.

Example 15 can include, or can optionally be combined with the subject matter of one or any combination of Examples 1 through 14 to optionally include an adapter coupling plate that can includes a first slot extending through from the third major surface to the fourth major surface and through which the first fastener extends.

Example 16 can include, or can optionally be combined with the subject matter of one or any combination of Examples 1 through 15 to optionally include a first fastener that can include a stop to prevent the adapter coupling plate from separating from the first fastener.

Example 17 can include, or can optionally be combined with the subject matter of one or any combination of Examples 1 through 16 to optionally include a second fastener extending from the mounting plate, wherein the first and second fasteners are threaded into the mounting plate and the adapter coupling plate is slidable along the first and second fasteners.

Example 18 can include, or can optionally be combined with the subject matter of one or any combination of Examples 1 through 17 to optionally include each of the first and second slide posts comprising: a shaft threadably engaged with the mounting plate; an engagement head located proximate the first major surface of the mounting plate; and a stop located proximate the fourth major surface of the adapter coupling plate.

Example 19 can include, or can optionally be combined with the subject matter of one or any combination of Examples 1 through 18 to optionally include a mounting plate that is slidably engaged with the adapter coupling plate via a tongue and groove system.

Example 20 can include, or can optionally be combined with the subject matter of one or any combination of Examples 1 through 19 to optionally include a tongue and groove system comprising: a pair of rails extending from the adapter coupling plate; and a pair of slots extending in the mounting plate.

Example 21 can include, or can optionally be combined with the subject matter of one or any combination of Examples 1 through 20 to optionally include a tongue and groove system comprising: a pair of rails extending from the mounting plate; and a pair of slots extending in the adapter coupling plate.

Example 22 can include, or can optionally be combined with the subject matter of one or any combination of Examples 1 through 21 to optionally include a third major surface of the adapter coupling plate that is spaced apart from the first major surface of the mounting plate.

Example 23 can include or use subject matter such as a system for aligning a prosthetic head component with a prosthetic stem, the system can comprise: a mounting plate; a slide post extending through the mounting plate in an adjustable manner; a prosthetic head component stationarily coupled to the mounting plate, the prosthetic head component having an access hole aligned with the slide post; and an adapter coupling plate slideably engaged with the mounting plate via the slide post; wherein the slide post can be adjusted from an exterior of the prosthetic head component through the access hole to immobilize the adapter coupling plate relative to the mounting plate.

Example 24 can include, or can optionally be combined with the subject matter of Example 23, to optionally include a set of size indicators located on the mounting plate; and a pointer located on the adapter coupling plate; wherein the pointer points to different size indicators as the adapter coupling plate slides against the mounting plate.

Example 25 can include, or can optionally be combined with the subject matter of one or any combination of Examples 23 or 24 to optionally include a slide post that can be adjusted to lock a position of the adapter coupling plate relative to the mounting plate.

Example 26 can include, or can optionally be combined with the subject matter of one or any combination of Examples 23 through 25 to optionally include a slide post that is threaded into the mounting plate, the slide post extending through a slot in the adapter coupling plate; a set of size indicators that comprise hash marks located on a surface of the mounting plate facing away from the prosthetic head; and a pointer that can comprise a portion of the adapter coupling plate that can align with each of the hash marks depending on a position of the adapter coupling plate relative to the mounting plate.

Example 27 can include or use subject matter such as a system for aligning a prosthetic head component with a prosthetic stem, the system can comprise: a mounting plate; a fastener extending from the mounting plate in an adjustable manner; a prosthetic head component stationarily coupled to the mounting plate, the prosthetic head component having an access hole aligned with the fastener; an adapter coupling plate; and a tongue and groove system slideably connecting the mounting plate and the adapter coupling plate; wherein the fastener can be adjusted from an exterior of the prosthetic head component through the access hole to immobilize the adapter coupling plate relative to the mounting plate.

Example 28 can include, or can optionally be combined with the subject matter of Example 27, to optionally include a set of size indicators located on the mounting plate; and a pointer located on the adapter coupling plate; wherein the pointer points to different size indicators as the adapter coupling plate slides against the mounting plate.

Example 29 can include, or can optionally be combined with the subject matter of one or any combination of Examples 27 or 28 to optionally include a fastener can be adjusted to bring the mounting plate closer to the prosthetic head component to squeeze the adapter coupling plate between the mounting plate and the prosthetic head component.

Example 30 can include, or can optionally be combined with the subject matter of one or any combination of Examples 27 through 29 to optionally include a collar extending from the adapter coupling plate, the collar including flanges to receive a neck of a stem adapter, wherein the flanges have a length that configures the flanges to be pushed into the prosthetic head component when the fastener is adjusted to bring the mounting plate closer to the prosthetic head component.

Example 31 can include, or can optionally be combined with the subject matter of one or any combination of Examples 27 through 30 to optionally include an adapter coupling plate and a mounting plate that are co-planar; and an adapter coupling plate that is thicker than the mounting plate.

Example 32 can include or use subject matter such as a method for aligning a prosthetic head component with a prosthetic stem, the method can comprise: attaching a mounting plate of a trialing device to a prosthetic head component, the trialing device further including an adapter coupling plate; inserting a neck of a prosthetic stem into the adapter coupling plate; sliding the mounting plate of the trialing device relative to the adapter coupling plate to a adjust a position of the prosthetic head component relative to the neck of the prosthetic stem; and from outside of the prosthetic head, adjusting a fastener connected to the mounting plate to immobilize a position of the adapter coupling plate to lock the position.

Example 33 can include, or can optionally be combined with the subject matter of Example 32, to optionally include sliding the adapter coupling plate against the fastener.

Example 34 can include, or can optionally be combined with the subject matter of one or any combination of Examples 32 or 33 to optionally include sliding slots of the adapter coupling plate along rails of the mounting plate.

Example 35 can include, or can optionally be combined with the subject matter of one or any combination of Examples 32 through 34 to optionally include inserting an instrument through the prosthetic head component to adjust the fastener and lock the position.

Example 36 can include, or can optionally be combined with the subject matter of one or any combination of Examples 32 through 35 to optionally include removing the trialing device from the neck; and reading a prosthetic size indication from the trialing device after adjusting the post and locking the position.

Example 37 can include, or can optionally be combined with the subject matter of one or any combination of Examples 32 through 36 to optionally include implanting the prosthetic stem component into a bone before inserting the neck of the prosthetic stem into the adapter coupling plate.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system for aligning a prosthetic head component with a prosthetic stem, the system comprising:
   a mounting plate comprising:
      a first major surface;
      a second major surface opposing the first major surface;
      an adapter accommodation hole extending through from the first major surface to the second major surface;
      a first hole extending through the mounting plate on a first side of the adapter accommodation hole;
      a second hole extending through the mounting plate on a second side of the adapter hole opposite the first hole; and
      sizing indicia located on the second major surface;
   a first fastener extending through the first hole of the mounting plate;
   a second fastener extending through the second hole of the mounting plate; and
   an adapter coupling plate slidably engaged with the mounting plate, the adapter coupling plate comprising:
      a third major surface that is planar facing in a direction of the first major surface;
      a fourth major surface that is planar opposing the third major surface;
      an adapter coupling hole extending through from the third major surface to the fourth major surface, the adapter coupling hole surrounded by the adapter accommodation hole;
      a first slot extending along the adapter coupling plate on a first side of the adapter coupling hole;
      a second slot extending along the adapter coupling plate on a second side of the adapter coupling hole opposite the first side; and
      an indicator located on the fourth major surface to point to various portions of the sizing indicia as the adapter coupling plate slides against the mounting plate at the first slot;
   wherein the first and second fasteners extend into the first and second slots to allow the adapter coupling plate and the mounting plate to slide against each other in relative up-and-down movement while limiting relative side-to-side movement.

2. The system of claim 1, further comprising the prosthetic head component, the prosthetic head component comprising:
   an outer curved surface for approximating an anatomic articulation surface of an anatomic head; and
   an inner surface having a cavity that accepts the first major surface of the mounting plate.

3. The system of claim 2, wherein the first fastener extends into the prosthetic head component so as to be accessible from the outer curved surface.

4. The system of claim 3, wherein the prosthetic head component includes a first access hole in the outer curved surface aligned with the first fastener.

5. The system of claim 2, further comprising a stem adapter, the stem adapter comprising:
   a body for engaging a socket of the prosthetic stem; and
   a neck extending from the body frictionally engaged with the adapter coupling hole and passing freely into the adapter accommodation hole.

6. The system of claim 5, further comprising the prosthetic stem, wherein the prosthetic stem comprises a humeral stem and the prosthetic head component comprises a humeral head.

7. The system of claim 2, further comprising a magnet located in the cavity to engage the first major surface of the mounting plate.

8. The system of claim 2, wherein the mounting plate is friction fit into the cavity of the prosthetic head component.

9. The system of claim 2, further comprising a first deformable sleeve to engage the first fastener.

10. The system of claim 2, wherein the outer curved surface of the prosthetic head component includes a rotational feature.

11. The system of claim 10, wherein the rotational feature comprises scallops disposed around a periphery of the outer curved surface.

12. The system of claim 10, wherein the rotational feature comprises a socket disposed in the outer curved surface.

13. The system of claim 2, wherein the inner surface of the prosthetic head component is textured to increase frictional engagement with bone.

14. The system of claim 1, wherein the first fastener is threaded into the mounting plate and passes through the adapter coupling plate.

15. The system of claim 14, wherein the first slot extends through from the third major surface to the fourth major surface.

16. The system of claim 15, wherein the first fastener includes a stop to prevent the adapter coupling plate from separating from the first fastener.

17. The system of claim 1, wherein the first and second fasteners are threaded into the mounting plate and the adapter coupling plate is slidable along the first and second fasteners.

18. The system of claim 17, wherein each of the first and second fasteners comprises:
a shaft threadably engaged with the mounting plate;
an engagement head located proximate the first major surface of the mounting plate; and
a stop located proximate the fourth major surface of the adapter coupling plate.

19. The system of claim 17, further comprising first and second elongate slots in which the first and second fasteners are configured to slide.

20. The system of claim 19, further comprising a wall extending from the adapter coupling hole, wherein the wall is shaped to receive a neck of a stem adapter of the prosthetic stem and the wall is positioned to slide within the adapter accommodation hole.

21. The system of claim 1, further comprising a flange projecting form the adapter coupling plate in the first direction, wherein the flange overlaps the sizing indicia, and wherein the indicator is located on the flange.

22. The system of claim 21, wherein the indicator comprises an arrow and the indicia comprises hash marks extending perpendicular to the first direction.

23. The system of claim 1, wherein the coupling plate further comprises a wall extending form the adapter coupling hole and configured to extend into the adapter accommodation hole.

24. The system of claim 1, wherein the first bore and the second bore do not extend through the adapter accommodation hole or the adapter coupling hole.

25. The system of claim 1, further comprising first and second stop nuts threaded onto the first and second fasteners.

26. The system of claim 1, wherein the adapter coupling hole comprises a through bore having opened ends.

27. A system for aligning a prosthetic head component with a prosthetic stem, the system comprising: a mounting plate comprising an adapter accommodation hole; a first hole extending through the mounting plate on a first side of the adapter accommodation hole; a second hole extending through the mounting plate on a second side of the adapter hole opposite the first hole; a first slide post extending through the first hole of the mounting plate; a second slide post extending through the second hole of the mounting plate; a prosthetic head component separate from the mounting plate and having a socket to removably receive the mounting plate in a fixed position, the prosthetic head component having an access hole aligned with said first and second slide posts, the access hole extending from an exterior convex surface of the prosthetic head component to an interior surface of the prosthetic head component; and an adapter coupling plate slideably engaged with the mounting plate via said first and second slide posts, the adapter coupling plate comprising: an adapter coupling hole aligned with the adapter accommodation hole; and a slot configured to receive said first and second slide posts; wherein said first and second slide posts can be adjusted from an exterior of the prosthetic head component through the access hole to immobilize the adapter coupling plate relative to the mounting plate; and a set of size indicators located on the mounting plate; and a pointer located on the adapter coupling plate; wherein the pointer points to different size indicators as the adapter coupling plate slides against the mounting plate.

28. The system of claim 27, wherein the slide post can be adjusted to lock a position of the adapter coupling plate relative to the mounting plate.

29. The system of claim 27, wherein:
the slide post is threaded into the mounting plate;
the slide post extends through a slot in the adapter coupling plate;
the set of size indicators comprise hash marks located on a surface of the mounting plate facing away from the prosthetic head; and
the pointer comprises a portion of the adapter coupling plate that can align with each of the hash marks depending on a position of the adapter coupling plate relative to the mounting plate.

* * * * *

UNITED STATES PATENT AND TRADEMARK OFFICE
CERTIFICATE OF CORRECTION

PATENT NO. : 11,083,588 B2  
APPLICATION NO. : 15/846624  
DATED : August 10, 2021  
INVENTOR(S) : Muir et al.

Page 1 of 1

It is certified that error appears in the above-identified patent and that said Letters Patent is hereby corrected as shown below:

In the Claims

In Column 27, Line 49, in Claim 23, delete "form" and insert --from-- therefor

Signed and Sealed this  
Nineteenth Day of October, 2021

Drew Hirshfeld  
*Performing the Functions and Duties of the*  
*Under Secretary of Commerce for Intellectual Property and*  
*Director of the United States Patent and Trademark Office*